(12) United States Patent
Insley et al.

(10) Patent No.: US 11,160,595 B2
(45) Date of Patent: Nov. 2, 2021

(54) SYSTEM, DEVICE AND METHOD FOR DELIVERY OF BIOMATERIALS FOR FRACTURE FIXATION

(71) Applicants: CelgenTek Limited, County Clare Shannon (IE); Kevin David Madden, Shannon (IE)

(72) Inventors: Gerard Michael Insley, Shannon (IE); Kevin David Madden, Shannon (IE); David Russell, Shannon (IE); Philip Procter, Shannon (IE); Carol O'Sullivan, County Limerick (IE); Kieran Murray, Shannon (IE)

(73) Assignee: CelgenTek Limited, County Clare Shannon (IE)

( * ) Notice: Subject to any disclaimer, the term of this patent is extended or adjusted under 35 U.S.C. 154(b) by 39 days.

(21) Appl. No.: 15/566,465

(22) PCT Filed: Apr. 15, 2016

(86) PCT No.: PCT/EP2016/058461
§ 371 (c)(1),
(2) Date: Oct. 13, 2017

(87) PCT Pub. No.: WO2016/166350
PCT Pub. Date: Oct. 20, 2016

(65) Prior Publication Data
US 2018/0132918 A1    May 17, 2018

Related U.S. Application Data

(60) Provisional application No. 62/147,718, filed on Apr. 15, 2015.

(51) Int. Cl.
*A61B 17/88* (2006.01)
*A61B 17/70* (2006.01)
(Continued)

(52) U.S. Cl.
CPC ...... *A61B 17/8833* (2013.01); *A61B 17/7098* (2013.01); *A61B 17/8816* (2013.01);
(Continued)

(58) Field of Classification Search
CPC ............ A61B 17/8805; A61B 17/8808; A61B 17/8825; A61B 17/8833; A61B 17/7098;
(Continued)

(56) References Cited

U.S. PATENT DOCUMENTS 3,760,503 A * 9/1973 Baskas ............... A61B 17/8825
433/90
4,538,920 A * 9/1985 Drake ................... B01F 5/0615
222/137
(Continued)

FOREIGN PATENT DOCUMENTS

CN        1835810        9/2006
CN       102740779      10/2012
(Continued)

OTHER PUBLICATIONS

"European Application Serial No. 16716612.3, Response filed May 30, 2018 to Office Action dated Nov. 22, 2017", 20 pgs.
(Continued)

*Primary Examiner* — Marcela I. Shirsat
(74) *Attorney, Agent, or Firm* — Schwegman Lundberg & Woessner, P.A.

(57) ABSTRACT

The invention relates to a delivery system, device and method for delivering biomaterials for fracture fixation (including augmented fixation), in particular, for delivery of bone cements. The mixing system ensures the biomaterial only commences setting upon extrusion from the mixer, cannula or during injection through an appropriate internal fracture fixation device, allowing for rapid closing by the surgeon. The system also permits the surgeon to cease
(Continued)

injecting the cement for an extended period of time before continuing the injection in another area using the same cartridge, through the simple removal of one mixer and attaching another in its place. The invention also provides a method of delivery of biomaterials to a desired implantation site.

15 Claims, 21 Drawing Sheets

(51) Int. Cl.
*A61B 17/86* (2006.01)
*B05C 17/005* (2006.01)
*B01F 15/00* (2006.01)
*A61B 17/00* (2006.01)

(52) U.S. Cl.
CPC ........ *A61B 17/8822* (2013.01); *A61B 17/864* (2013.01); *A61B 17/8805* (2013.01); *A61B 17/8811* (2013.01); *A61B 17/8825* (2013.01); *A61B 2017/00495* (2013.01); *A61B 2017/8838* (2013.01); *B01F 15/0087* (2013.01); *B01F 2215/0039* (2013.01); *B05C 17/00553* (2013.01); *B05C 17/00566* (2013.01)

(58) Field of Classification Search
CPC ............ A61B 17/8816; A61B 17/8822; A61B 17/8811; A61B 17/7097; A61B 2017/00495; A61B 2017/8838; B05C 17/00553; B05C 17/00566; B05C 17/00596; B05C 17/0103; B01F 13/0023; B01F 15/0087; B01F 15/0237; B01F 2215/0039; B01F 2215/0027; B01F 5/0602; B01F 5/0615
USPC ..... 606/92–95, 86 R; 604/11–18, 57–60, 82, 604/84, 89; 433/87, 89, 90; 222/15.5, 222/145.4, 145.6; 366/96–99, 117, 366/241–245, 341, 602
See application file for complete search history.

(56) References Cited

U.S. PATENT DOCUMENTS

| | | | | |
|---|---|---|---|---|
| 5,333,760 | A * | 8/1994 | Simmen | B05C 17/00506 222/137 |
| 6,648,852 | B2 * | 11/2003 | Wirt | A61B 17/00491 604/191 |
| 8,231,632 | B1 | 7/2012 | Jordan et al. | |
| 8,366,717 | B1 | 2/2013 | Jordan et al. | |
| 2003/0083662 | A1 | 5/2003 | Middleton | |
| 2004/0267272 | A1 | 12/2004 | Henniges et al. | |
| 2005/0101963 | A1 | 5/2005 | Merboth et al. | |
| 2006/0293664 | A1 | 12/2006 | Schumacher | |
| 2007/0270858 | A1 * | 11/2007 | Trieu | A61B 17/7098 606/279 |
| 2009/0131950 | A1 | 5/2009 | Liu et al. | |
| 2010/0030135 | A1 * | 2/2010 | Mitchell | A61M 31/00 604/48 |
| 2011/0060373 | A1 * | 3/2011 | Russell | A61B 17/8057 606/304 |
| 2011/0106054 | A1 * | 5/2011 | Osborne | A61B 17/8816 604/518 |
| 2011/0208238 | A1 | 8/2011 | Hoffman | |
| 2014/0324013 | A1 * | 10/2014 | Shadeck | A61B 17/8822 604/500 |
| 2014/0378937 | A1 | 12/2014 | Anderson et al. | |
| 2015/0073423 | A1 | 3/2015 | Hoefer et al. | |

FOREIGN PATENT DOCUMENTS

| | | |
|---|---|---|
| CN | 107743383 | 2/2018 |
| JP | 2002355317 A | 12/2002 |
| JP | 2005515780 A | 6/2005 |
| JP | 2013520242 A | 6/2013 |
| JP | 2018515301 | 6/2018 |
| WO | 9944509 | 9/1999 |
| WO | WO-2005016170 A2 | 2/2005 |
| WO | 2013188354 | 12/2013 |
| WO | WO-2014149746 A1 | 9/2014 |
| WO | WO-2014152742 A2 | 9/2014 |
| WO | WO-2016166350 A2 | 10/2016 |

OTHER PUBLICATIONS

"International Application Serial No. PCT/EP2016/058461, International Search Report dated Oct. 28, 2016", 7 pgs.
"International Application Serial No. PCT/EP2016/058461, Invitation to Pay Additional Fees and Partial Search Report dated Jul. 20, 2016", 7 pgs.
"International Application Serial No. PCT/EP2016/058461, Written Opinion dated Oct. 28, 2016", 21 pgs.
"European Application Serial No. 16716612.3, Communication Pursuant to Article 94(3) EPC dated Oct. 11, 2019", 4 pages.
"Chinese Application Serial No. 201680034742.3, Office Action dated Oct. 23, 2019", with English translation, 16 pages.
"Australian Application Serial No. 2016249965, First Examination Report dated Mar. 23, 2020", 4 pgs.
"Chinese Application Serial No. 201680034742.3, Response filed Feb. 20, 2020 to Office Action dated Oct. 23, 2019", (English Translation of Claims), 11 pgs.
"European Application Serial No. 16716612.3, Response filed Apr. 6, 2020 to Communication Pursuant to Article 94(3) EPC dated Oct. 11, 2019", 6 pgs.
"Japanese Application Serial No. 2018-505539, Notification of Reasons for Refusal dated Mar. 17, 2020", (W/ English Translation), 17 pgs.
"Chinese Application Serial No. 201680034742.3, Office Action dated May 12, 2020", with English translation, 15 pages.
"Japanese Application Serial No. 2018-505539, Response filed Jun. 17, 2020 to Notification of Reasons for Refusal dated Mar. 17, 2020", with English claims, 31 pages.
"European Application Serial No. 16716612.3, Communication Pursuant to Article 94(3) EPC dated Jul. 3, 2020", 7 pages.
"Chinese Application Serial No. 201680034742.3, Response filed Jul. 10, 2020 to Office Action dated May 12, 2020", (W/ English Translation of Claims), 19 pgs.
"Japanese Application Serial No. 2018-505539, Final Notification of Reasons for Refusal dated Jul. 14, 2020", (W/ English Translation), 5 pgs.
"Chinese Application Serial No. 201680034742.3, Response filed Jan. 21, 2021 to Office Action dated Nov. 23, 2020", with English claims, 9 pgs.
"Japanese Application Serial No. 2018-505539, Response filed Oct. 1, 2020 to Final Notification of Reasons for Refusal dated Jul. 14, 2020", with English claims, 17 pages.
"European Application Serial No. 16716612.3, Response filed Nov. 9, 2020 to Communication Pursuant to Article 94(3) EPC dated Jul. 3, 2020", 15 pages.
"Chinese Application Serial No. 201680034742.3, Office Action dated Nov. 23, 2020", with English translation, 16 pages.
"Australian Application Serial No. 2016249965, Response filed Mar. 4, 2021 to First Examination Report dated Mar. 23, 2020", 31 pgs.
"Australian Application Serial No. 2016249965, Subsequent Examiners Report dated Mar. 17, 2021", 3 pgs.
"Australian Application Serial No. 2016249965, Response filed Mar. 19, 2021 to Subsequent Examiners Report dated Mar. 17, 2021", 16 pgs.

(56) References Cited

OTHER PUBLICATIONS

"Chinese Application Serial No. 201680034742.3, Decision of Rejection dated May 17, 2021", (W/ English Translation), 18 pgs.

* cited by examiner

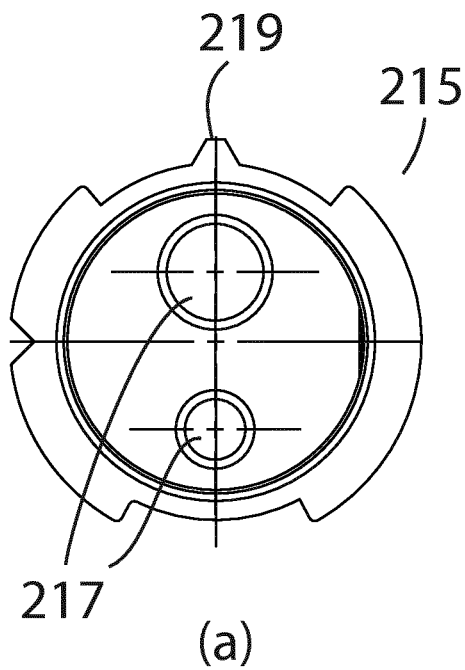
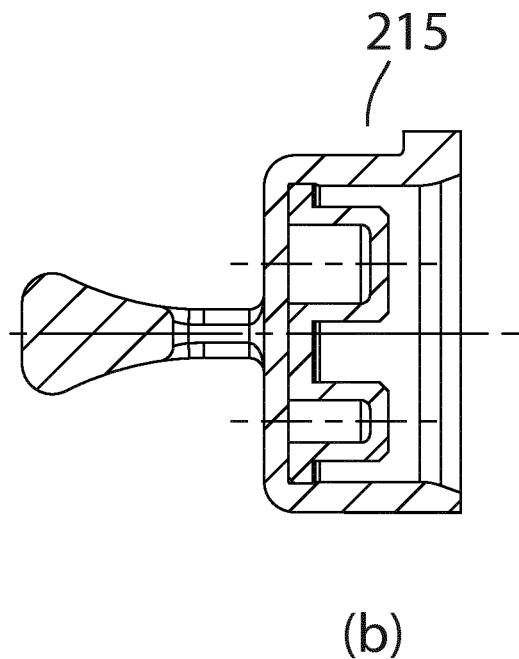
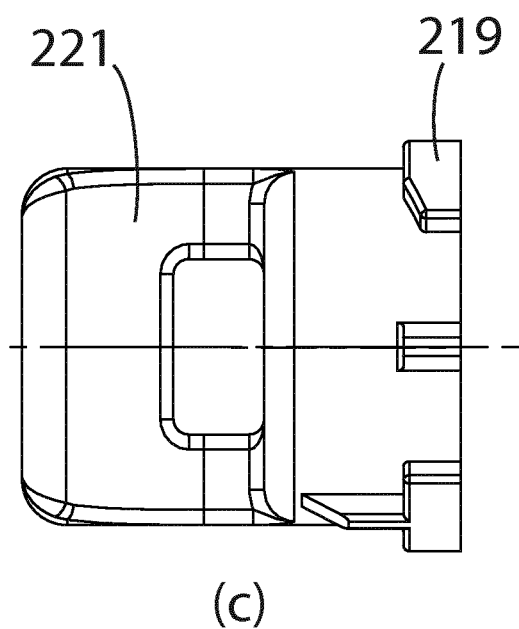
Fig. 6

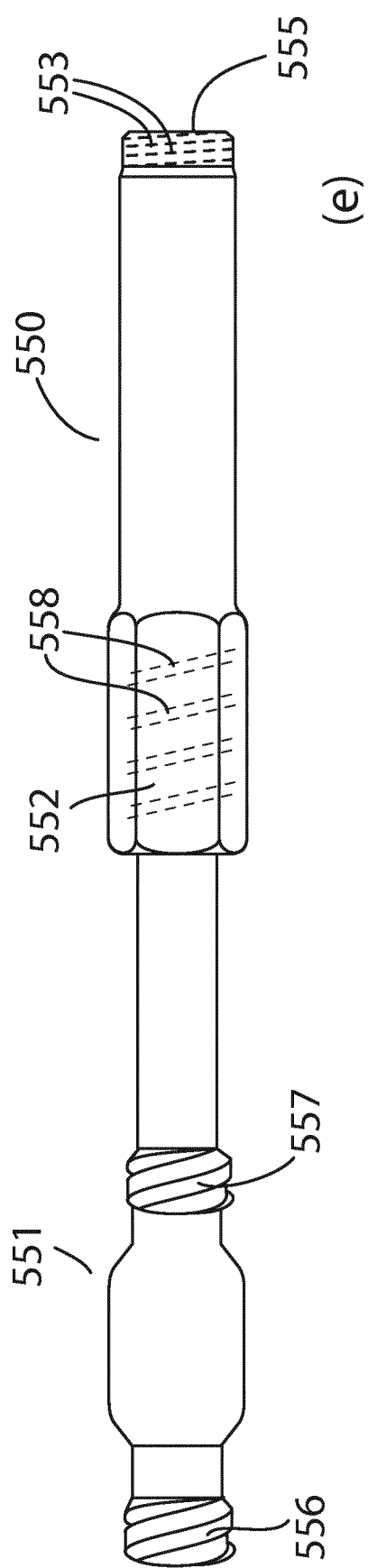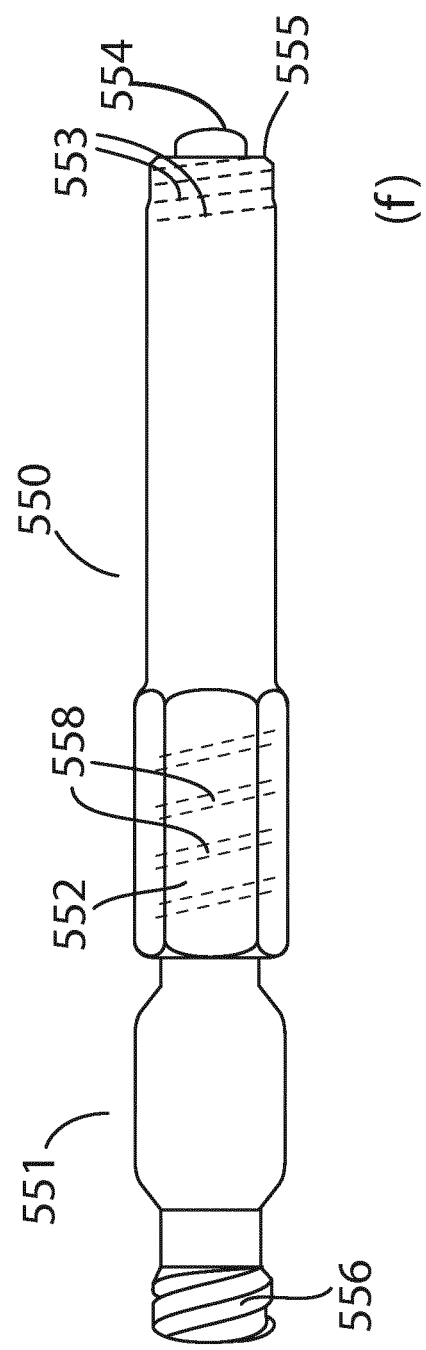
Fig.11

(a)

SYSTEM, DEVICE AND METHOD FOR DELIVERY OF BIOMATERIALS FOR FRACTURE FIXATION

This application is a U.S. National Stage Application under 35 U.S.C. 371 from International Application Serial No. PCT/EP2016/058461, filed on Apr. 15, 2016, and published as WO 2016/166350 A2 on Oct. 20, 2016, which claims priority to U.S. Patent Application Ser. No. 62/147,718, filed on Apr. 15, 2015, the benefit of priority of each of which is claimed hereby, and each of which are incorporated by reference herein in its entirety.

FIELD OF THE INVENTION

The present invention relates to a system and device for delivery of biomaterials for fracture fixation and to a method of delivering biomaterials for fracture fixation including augmented fixation.

BACKGROUND OF THE INVENTION

The current standard method for delivering bone void substitutes ('biomaterials'), such as injectable calcium phosphate cements, does not permit the user (typically, the user is a surgeon) to operate within a comfortable timeframe. Currently, the known systems require manual mixing of the biomaterials before loading into a syringe-type device for delivery. This manual mixing step begins the curing (setting) process for the biomaterials and has the serious drawback that the surgeon has an extremely limited timeframe (sometimes of the order of 120 seconds) in which he/she must place a biomaterial, that is undergoing a setting process, into the known delivery system and then deliver the material, rapidly (again often within 2 minutes), to the site of implantation. These known systems can lead to difficulties during surgery, culminating in inadequate or restrictive delivery of the biomaterial implant.

To overcome the difficulties above, premixed cements have recently become available. However, those currently available for broad trauma and orthopaedic indications are not desirable as they can take long periods of time to set sufficiently and/or the entire dose of premixed cement must be delivered immediately, once the dispensing process is initiated. Again, these known systems can lead to difficulties during surgery, culminating in inadequate or restrictive delivery of the biomaterial implant.

The present invention seeks, as an aim, to alleviate the disadvantages of the prior art.

Features of the present invention are set out in the appended Claims of the present invention. Advantageous features are included in the dependent Claims.

The present invention provides a biomaterial delivery system with a highly effective seal provided at each connection between the delivery device, reservoir for containing the biomaterial(s) and any activation component that may be included, the mixer device and the conduit for transferring the biomaterial(s) from the mixer device to the desired site. It is to be understood that the mixer device may comprise a cannula with or without mixing element comprised in the mixer device. The mixing of the biomaterial(s) may occur in the mixing device and may also occur in the conduit. In one embodiment, the conduit comprised mixing elements; in that embodiment, the conduit comprises a cannula including mixing elements. The mixing elements may be fixed at one end of the conduit or preferably, the mixing elements are movable along the length of the conduit (cannula or internal fracture fixation device). The moveable mixing elements may be able to move in both directions along the length of the conduit, that is the moveable mixing elements may be adapted for reciprocating movement along the length of the conduit. In accordance with the present invention, the configurations 2, 3 and 4 (shown in FIGS. 13, 14 and 15) are especially advantageous whereby, biomaterial expiry (shelf life) is maximized for a far longer time, up to several months, by using the system of the present invention in the Configuration 2, 3 and 4 of the system as will be described herein below.

The biomaterial delivery system, device and method of the present invention has the advantage that it allows simple and effective delivery of a biomaterial to a target site, for augmenting fracture fixation without putting any time constraints on the user/surgeon. The system, device and method of the present invention also has the advantage that no curing reaction occurs until injection begins, (in a preferred embodiment, through the mixing tip of a mixer device of the system of the present invention) i.e. the curing reaction takes place during delivery to the implantation site and not before delivery. Furthermore, by simply exchanging the mixer device included in the delivery system of the present invention, the surgeon gains the advantage and flexibility of having a 'start/stop' ability that allows recommencement of delivery of the biomaterial up to 2 hours after initial use. The delivery system and device of the present invention is suitable for delivering many different biomaterials and also is capable of connecting to, and specifically adapted to engage with, internal fracture fixation devices such as screws, nails and pins. The internal fracture fixation device may comprise a conduit which may extend along an elongate longitudinal axis of the internal fracture fixation device so that the internal fracture fixation device is in fluid communication with a reservoir of biomaterial(s) so that, in use, the biomaterial(s) can be delivered from the reservoir through the mixer device and through the conduit of the internal fracture fixation device. The conduit may also be provided axially about the internal fracture fixation device by providing apertures axially about the circumference of the internal fracture fixation device, optionally, axially about the ridges of the threads of the internal fracture fixation device where the internal fracture fixation device comprises screw threaded arrangement, partially or extending fully along the longitudinal axis of the internal fracture fixation device.

BRIEF SUMMARY OF THE INVENTION

The biomaterial delivery device of the present invention comprises a dispenser device, optionally, in a preferred embodiment, the dispenser device is in the form of a dispenser gun; a sealable reservoir of biomaterial, the sealable reservoir, optionally, in the preferred embodiment, being in the form of a cartridge having at least one sealable chamber; a mixer device; and a conduit for transferring the biomaterial(s) from the reservoir to the desired delivery site. In one embodiment, the conduit comprises a cannula. In an alternative embodiment, the conduit comprises an internal fracture fixation device. The dispenser device, optionally, in the form of a dispenser gun, is configured to discharge the biomaterial and an activation component (if required) from the reservoir into the mixer device and the conduit, before being delivered to the implantation site. A benefit of the system and device of the present invention is that the system and device enhance the mechanical forces needed to successfully deliver biomaterials, typically, by extruding the biomaterials, which may be, and indeed typically are, of high viscosity, from the overall device, while minimizing the effort needing to be exerted by the user who is typically, a surgeon.

In one embodiment, the dispenser device is in the form of a dispenser gun and the reservoir comprises a cartridge; the dispenser gun comprising a cartridge support for supporting the cartridge for containing the reservoir of biomaterial.

In one embodiment, the cartridge support may comprise a slot configured for engaging with the biomaterial-containing cartridge. The delivery device may also comprise an activation device which may be provided as an actuation trigger which is operable to advance a plunger drive mechanism in order to release the biomaterial from the reservoir/cartridge. Ideally, a first plunger is associated with a first chamber of the cartridge and a second plunger is associated with a second chamber of the cartridge. One or more plunger drive mechanisms may be associated with the first and second plungers. In a preferred embodiment, the actuation mechanism is provided as a trigger mechanism operable by a user's hand. Once the trigger is actuated, a gripper plate engages with the plunger drive mechanism and the plunger drive mechanism advances the first plunger into the first chamber; and may also advance the second plunger into the second chamber if a second chamber is provided in the reservoir; the movement of the or each plunger urges the biomaterial out of the or each chamber of the cartridge. The dispenser gun comprises a release button that allows the user/surgeon to manually retract the plungers if required in order to remove the cartridge. The cartridge unit typically comprises two or more chambers, a first chamber providing containment of the biomaterial and a second chamber comprising an activator component (if needed) or another biomaterial so that each chamber provides containment of the first biomaterial and any activator component separately until required for delivery at the site of the surgery.

In an alternative embodiment, the cartridge unit may comprise three or more chambers depending on the biomaterial formulation. Each chamber of the reservoir cartridge comprises a sealable enclosure of generally cylindrical cross section having an elongated longitudinal axis, and the cylinder having proximal and distal ends. The or each chamber comprises a piston/plunger, which, are generally positioned at the proximal end of the cartridge. A stopping member is located at the proximal end on the cylindrical wall of the cartridge to prevent the piston/plunger from being pushed outside the housing. A seal such as a foil seal or a bung or similar sealing means may be fixated at the proximal end of the cartridge to support containment, whereby the user/surgeon can remove this seal before usage of the device. The distal end of the cartridge comprises feeding channels that are in fluid communication with the mixer. The number of channels is generally governed by the number of chambers included in the cylinder unit of a particular embodiment of the device of the present invention so that each chamber may have its own channel in fluid communication with the mixer. Each of the channels can either be sealed via ultrasonic weld, foil seal, bung cap or by similar sealing device in order to provide appropriate containment before usage. The surgeon will be able to remove this seal manually from each of the channels in order to expose the contents of any of the channels before placement of the mixer prior to delivery of the biomaterial. All components of the cartridge are manufactured using medical grade polymeric materials that have excellent moisture/oxygen barrier characteristics specific to the biomaterial contained within.

In one embodiment, the mixer device comprises a generally cylindrical shaft having proximal and distal ends. The mixer device comprises a mixer section between the proximal and distal ends of the mixer. At the proximal end, a specially adapted connector allows the mixer to be attached to a cartridge that comprises two or more chambers to support the delivery of the components to the mixing section of the mixer device. The interface between the cartridge and mixer is designed so that a high quality seal is created to prevent loss/leakage of the biomaterials or activator components. At the distal end of the mixer, a Luer lock permits connection of the system to cannulas or other internal fracture fixation devices such as cannulated screws, nails and pins. The mixing section typically comprises mixing elements such as a helical baffle or similar mixing elements. The mixing elements may be provided in multiple configurations to enable mixing and delivery of different viscosity biomaterials. The biomaterials are mixed by moving them through the mixer section of the mixer device where the biomaterial and activator component are brought together. At this mixing stage, the curing reaction is initiated, forming the required material at exactly the point of dispensing, allowing the surgeon to have full control of the setting reaction. The system of the present invention provides mixer devices in a number of embodiments of the mixer device, each of which is adapted to be suitable for use with biomaterial(s) of differing viscosity. In one embodiment, the mixer device may comprise mixing elements; optionally, the mixing elements may be located throughout substantially the full length of the mixer shaft; and may or may not be fixated to the proximal end of the mixer. The delivery system of the present invention in the first embodiment (the delivery system in the first embodiment is also referred to herein as Configuration 1) is typically used for biomaterials that have low viscosities and the delivery device in this embodiment, and are adapted to be capable of mixing the components up to 65,500 times.

For high viscosity biomaterials, the mixer device may comprise a mixer shaft comprising a lesser number of mixing elements. In an alternative embodiment, the mixing elements may be arranged such that they are not fixed and are free to move along the full length of the mixer shaft or substantially the full length of the mixer shaft. The movement of the mixing elements is possible in both directions partially or fully along the length of the mixer device. In a further alternative embodiment, the mixing elements may be fixated to the proximal end of the mixer shaft (the delivery system in the second embodiment is also referred to herein as Configuration 2). When high viscosity biomaterials and activator components are dispensed into the mixer shaft containing the mobile mixing elements, the biomaterials and activator components have time to partly mix before being pressurized against the mixing elements at the distal end, which completes the mixing process. This helps to reduce the viscosity of the components, therefore, allowing them to flow more freely through the mixing elements. By doing so, the injectability force is reduced significantly, thus, enhancing the usability of the device.

In a further alternative embodiment, a third configuration (the delivery system in the third embodiment is also referred to herein as Configuration 3) the present invention provides a delivery device for high viscosity biomaterials comprising a number of mobile mixing elements in a mixing device having a mixer shaft of extended length relative to the length of the mixer device of the previous embodiments. when the biomaterial(s) and any activation component enters the mixing shaft from the cartridge, they have additional time to partly mix before reaching the mixing elements at the distal end. This helps to reduce the viscosity of the components further, allowing them to flow more freely through the mixing elements. Where a longer length mixing device is included in the system of the present invention, a cannula that is of shorter length, for example, a cannula of 50 mm, than in other embodiments of the present invention, may be used.

In a further alternative embodiment, (the delivery system in the fourth embodiment is also referred to herein as Configuration 4) for extremely high viscosity biomaterials, the mixer device comprises a mixer shaft without any mixing elements; thus in this embodiments, the mixing elements are removed completely from the mixing shaft. In this embodiment, the components are mixed at a later stage, such as in the cannula device or other internal fracture fixation devices such as cannulated screws including fenestrated screws, nails and pins that may be included in the system of the present invention. By removing the mixing elements entirely from the mixer, this allows the biomaterial and activator components to partly but sufficiently mix and reduce their viscosities before exiting the mixer. The cannula is comprised of a cylindrical tube having both proximal and distal ends with an internal diameter of 2.55 mm and an outer diameter of 3.5 mm (other diameters may be required depending on the biomaterial to be dispensed). At the proximal end, the cannula has a male Luer lock which can fit securely on to the female Luer lock of the mixer. In addition, this end of the cannula includes two wings to allow the surgeon to secure the cannula to the mixer with ease. At the distal end of the cannula, this is where the final mixed biomaterial is dispensed from the complete device into the target area. The distal end can have a round nose tip with an opening of 1.5 mm or a flat tip with an opening of 2.5 mm. A flat tip is typically used where the mixing elements are included in the mixer. When there are no mixing elements in the mixer, the mixing elements are typically placed in the cannula. A round nose tip cannula is used in this case to prevent the mixing elements from being moved out of the cannula housing as the biomaterials and activator components are being dispensed. The purpose of moving the mixing elements from the mixer to the distal end of the cannula is to allow the biomaterials and activator components to come together for an extended period of time prior to reaching the elements. This helps to reduce the viscosity by partially mixing the components, therefore; allowing them to flow more freely through the mixing elements. In terms of design, the reduction of the internal diameters from the mixer to the cannula aids the mixing process, due to the turbulence created at this section. In addition, the reduction of the internal diameter increases the velocity of the components, thus, reducing the overall pressure in contrast to the alternative systems previously mentioned. One of the principle design features that influences the pressure gradients across previous mentioned systems is the positioning of the mixing elements within the device. By having them positioned at an early stage in the device, this hinders viscosity reduction of the components while creating a flow barrier prior to reaching the reduced internal diameters between the mixer and cannula. This reduces the velocity of the components in the system, therefore; increasing the pressure. The working length of the cannula can vary in size depending on the viscosity of the biomaterial and the surgeon requirements. Having a cannula with a longer working length allows the biomaterial and activator component more time to mix before being dispensed to the target area and this applies for all aforementioned systems. In the embodiment of the system where the mixer device contains no mixing elements and the cannula comprises mixing elements at the distal end, providing a longer cannula than would be used in other embodiments of the present invention, allows the viscosity of the components to decrease substantially over the length of the cannula, therefore; enhancing the injectability for the surgeon. The length of the mixer device can also vary. Generally, embodiments of the system of the present invention comprising a mixer device having a relatively longer length may comprise a cannula having a relatively shorter length, relative to other embodiments of the present invention. So, for example, 50 mm, and embodiments having shorter mixing elements may have longer cannulas of, for example, 100 mm. These modifications aim to maintain a consistent distance between the dispenser gun and the target site. This ensures proper mixing and is also convenient for the surgeon as the hands may be kept at an optimum distance during procedures.

The surgeon has the option to connect the mixer devices of each of the embodiments of the present invention as described about in configurations 1-4, to a cannula for bone void filling or to any number of a multiple internal fracture fixation devices for augmented fixation trauma and orthopaedic indications (i.e. to be used without the cannula component). A detailed explanation is already provided above for the overall functionality of the cannula option. For the internal fracture fixation devices such as cannulated (fenestrated) screws, pins, nails or similar, they have the ability to be connected to each mixer configurations by the use of a sheath and sheath adaptor (provided with the internal fracture fixation device). At the distal end of the sheath is a standard screwing thread that allows the surgeon to fasten the sheath onto the internal fracture fixation device by screwing in a clockwise direction. At the proximal end of the sheath is a female Luer lock that permits connection of the sheath to the sheath adaptor. The distal end of the sheath adaptor is placed inside the proximal end of the sheath. When the sheath adaptor is fastened in place by screwing in a clockwise direction, the distal end of the device protrudes past the distal end of the sheath and into the cannula opening of the proximal end of the internal fracture fixation device. At the proximal end of the sheath adaptor is a male Luer lock that allows the overall device (sheath, sheath adaptor and internal fracture fixation device) to be connected to any of the mixers in configurations 1-4. With the mixer in configurations 1-3, mixing of the biomaterials with the activator components is completed prior to entering the sheath adaptor and internal fracture fixation device. For the mixer in Configuration 4, the biomaterials and activator components are mixed to completion upon entering the internal fracture fixation device. In this design, the complete mixing process occurs further in the system as the components travel through the various contours of the sheath adaptor and the cannulated internal fracture fixation device. These contours create sufficient turbulence to homogeneously mix the components to provide the required setting time and compressive strength characteristics.

First of all, the sheath is fastened onto the internal fracture fixation device by screwing the sheath in a clockwise direction. The distal end of the sheath adaptor is then placed inside the sheath from the top end.

The four parts can be assembled very quickly within the operating theatre at any point prior to use of the system. The biomaterial fracture fixation system is a 'point and shoot' set-up, whereby the mixer is attached in one step and, if required, a cannula, the trigger is squeezed on the dispenser gun for simple delivery at the target site. The system also permits a "stop-start" feature. Once injection has stopped, injection may recommence within a short period (approx 30 seconds) without mixer exchange or up to 2 hours later by removing the used mixer and replacing it with a fresh one.

This system is capable of delivering any required biomaterial, provided it is formulated to flow through the mixer and cannula systems. The dispenser gun provides a significant mechanical advantage to the surgeon, providing 5.5× the force to the cartridge over that which the surgeon puts on the dispenser gun. This allows the surgeon to inject biomaterials in a manner that is not possible using more traditional systems.

BRIEF DESCRIPTION OF THE DRAWINGS

The present application will now be described, by way of example only, with reference to a number of alternative embodiments which are shown in the accompanying drawings in which:

FIG. 6a is a rear view of a cartridge cap for sealing the proximal end of the cartridge opposed from the feeding channels which are provided at the distal end of the cartridge in use; FIG. 6b is a side view of the cartridge cap of FIG. 6a and FIG. 6c is a rotated side view of the cartridge cap;

FIG. 7a is a perspective view of one embodiment of a piston according to the invention, operable to discharge biomaterial(s) and any activation component (if needed) from the or each chamber of the cartridge; FIG. 7b is a side view of the piston and FIG. 7c is a cross section of the piston of FIG. 7a;

FIG. 8a is a perspective view of a piston in an alternative embodiment of the invention; FIG. 8b is a side view of the piston of FIG. 8a; and FIG. 8c is a cross section of the piston of FIG. 8a;

FIG. 9a is a front view of a first embodiment of a mixer device according to the invention; FIG. 9b is a longitudinal cross sectional view of the mixer device of FIG. 9a;

FIG. 10a is a side view of a cannula for connecting with the mixer device of FIGS. 9a and 9b; FIG. 10b is a longitudinal section of the cannula of FIG. 10a;

DETAILED DESCRIPTION OF THE INVENTION WITH REFERENCE TO THE DRAWINGS

Figure 1:
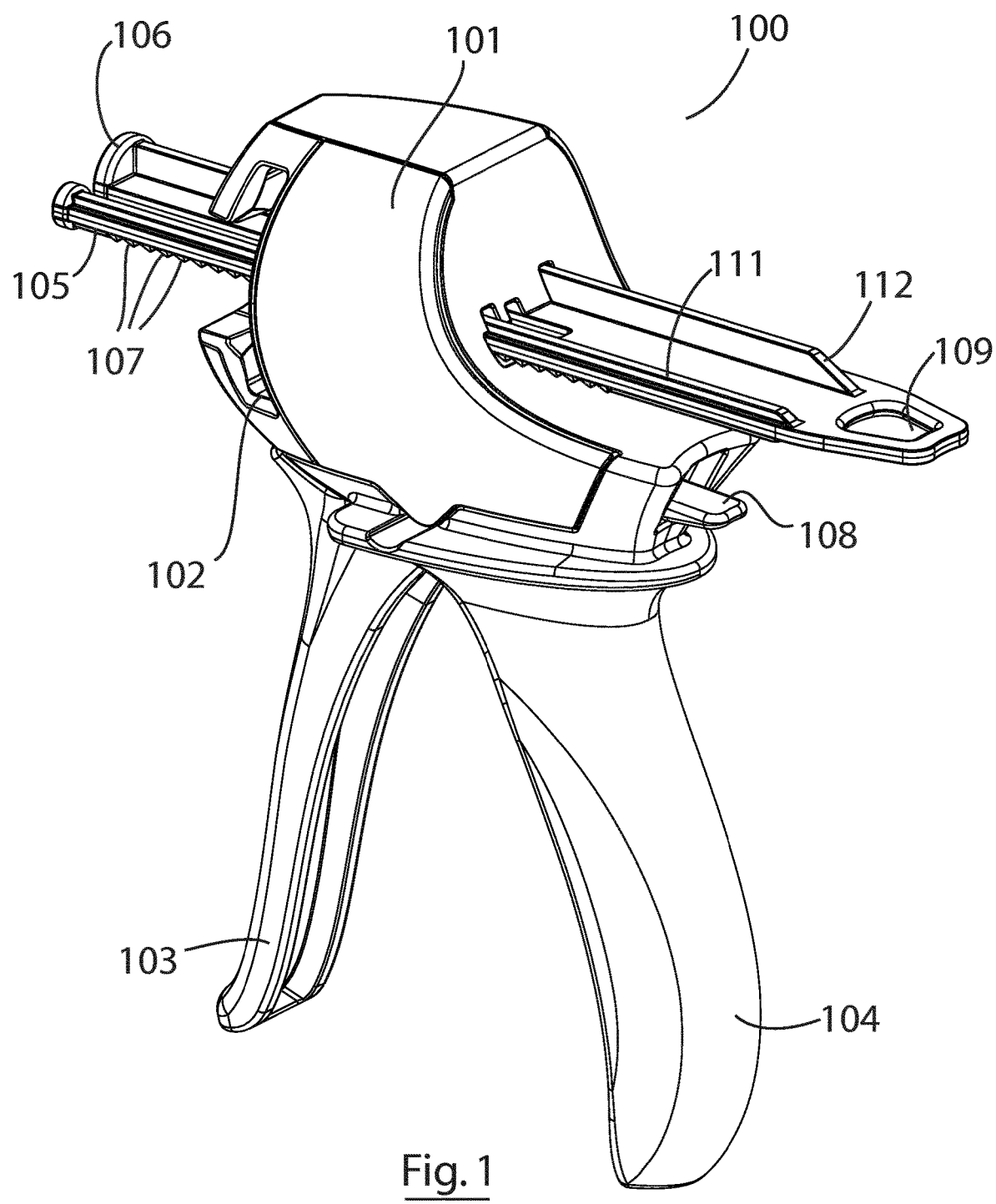
FIG. 1 is a perspective view of a dispenser device in the form of a dispenser gun according to one embodiment of the present invention.
Figure 2:
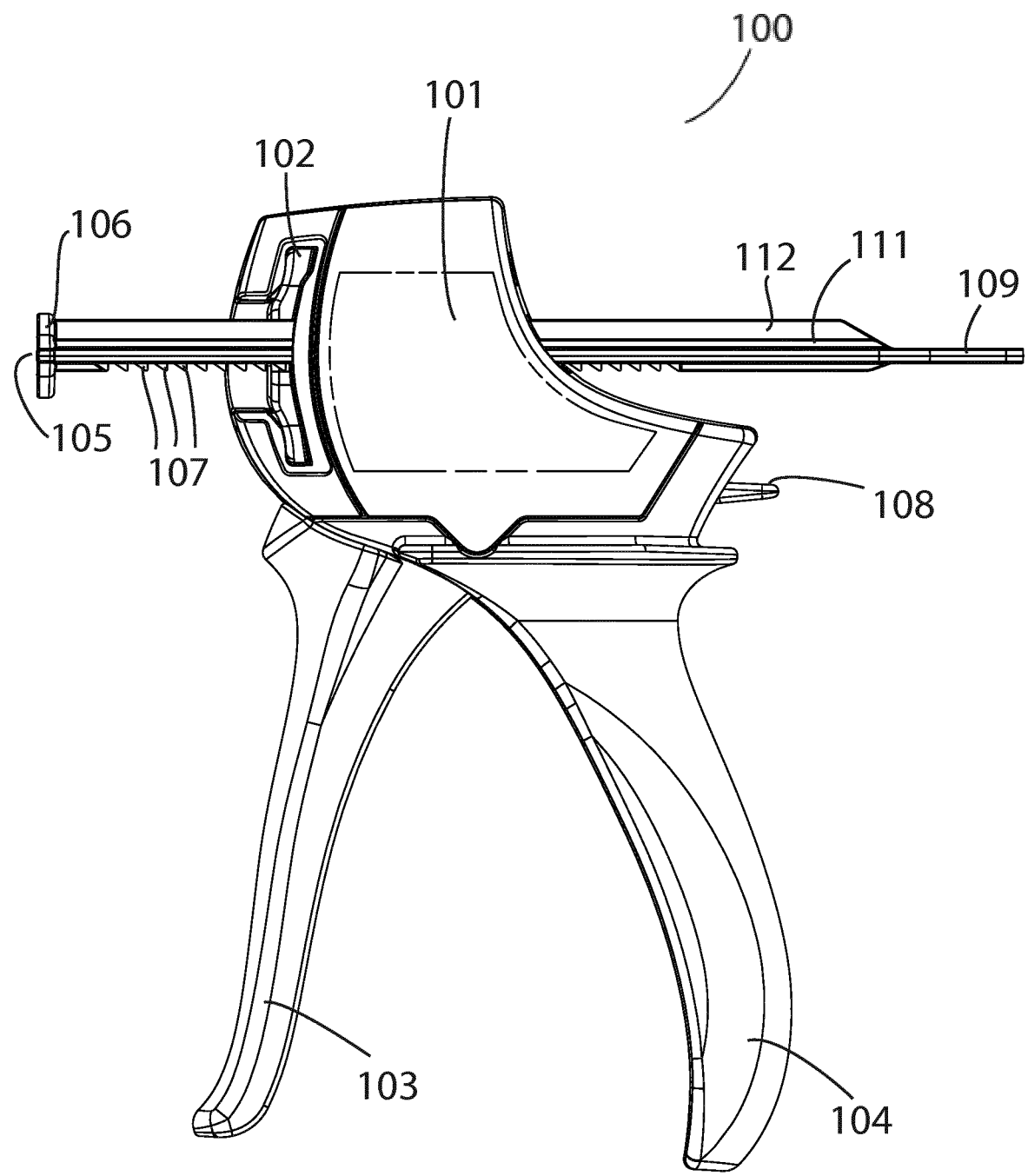
FIG. 2 is a side view of the dispenser device of FIG. 1.
Figure 3:
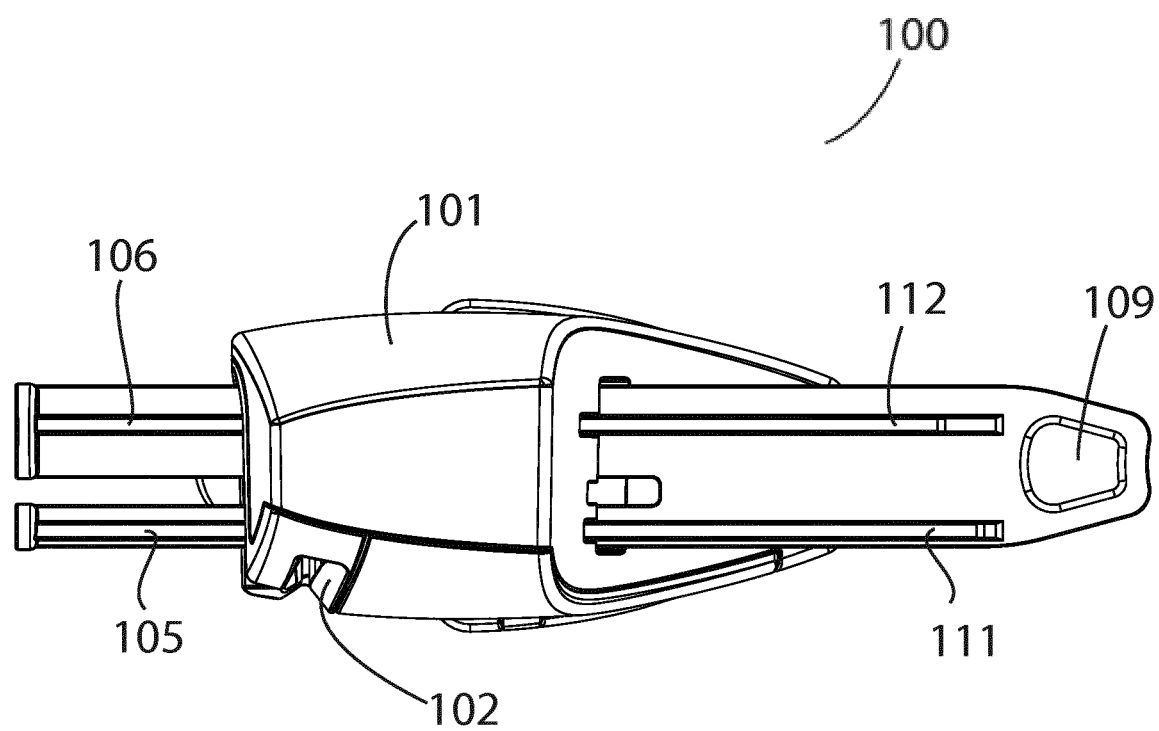
FIG. 3 is a top view of the dispenser device of FIG. 1.
Figure 18:
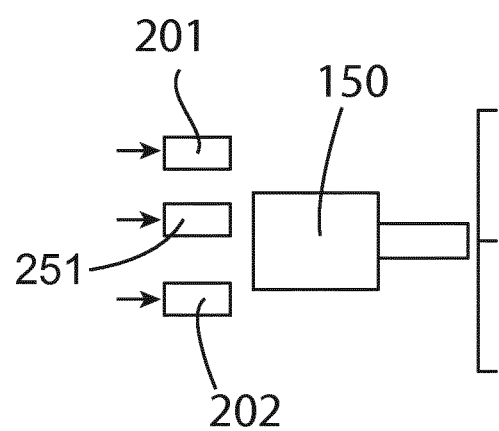
FIG. 18a is a schematic drawing of an alternative embodiment of the invention having three biomaterial components.
FIG. 18b is a longitudinal section of an alternative embodiment of a cartridge having three cylinders.
FIG. 18c is a top view of an alternative embodiment of a dispenser gun having three biomaterial components.
Figure 18:
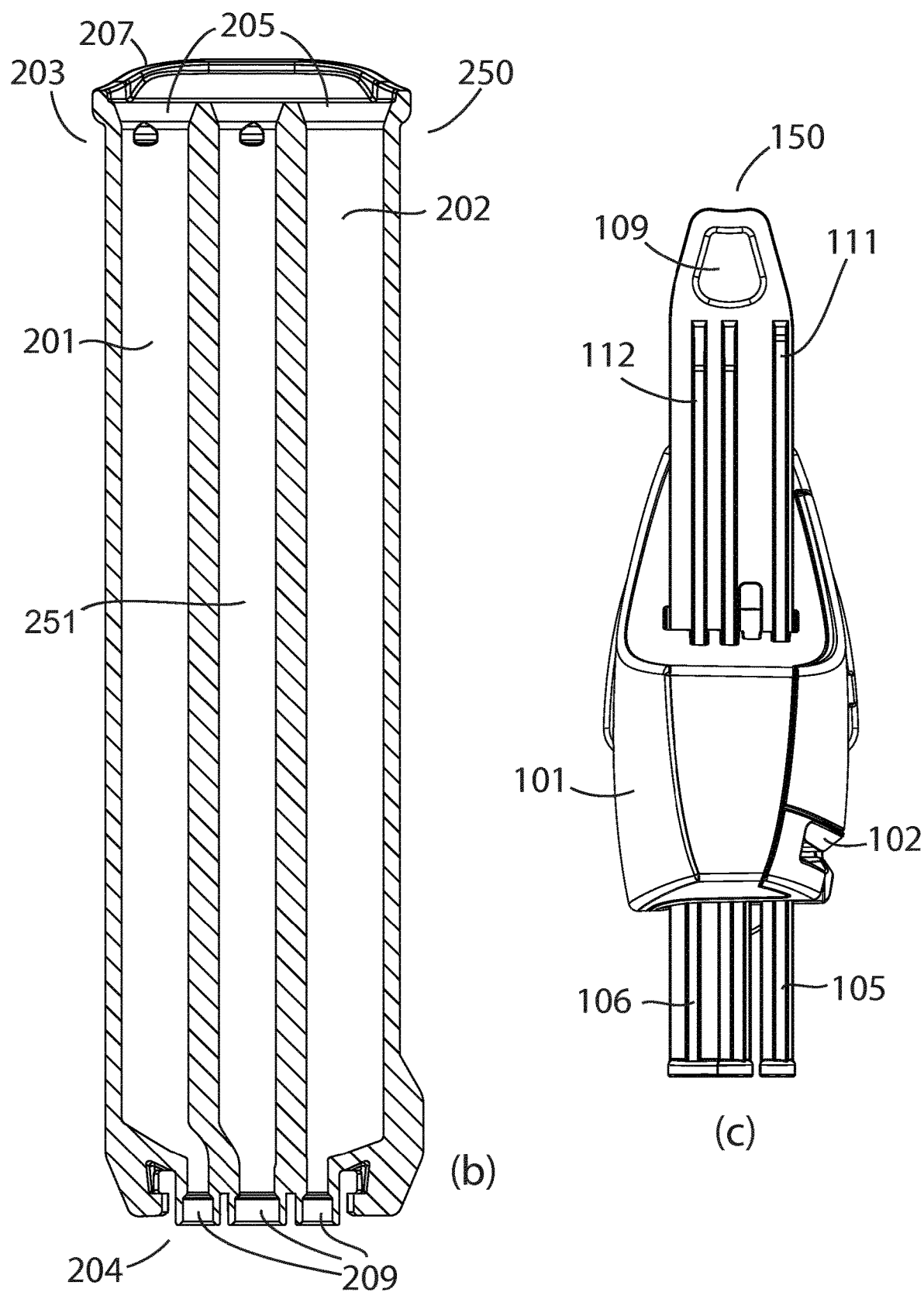

The present invention will now be described, more particularly, with reference the accompanying drawings and the following reference numerals are used to indicate parts of the delivery device of the present invention. Like parts are indicated by like reference numerals:

100 dispenser gun
101 housing of dispenser gun
102 tailored slot for cartridge
103 trigger
104 stationary handle
105 plunger
106 plunger
107 gripper plate teeth
108 release button
109 second slot
111 gripper plate guide
112 second gripper plate guide
150 Alternative embodiment of dispenser gun (FIG. 18)
200 cartridge 201 first chamber of cartridge 200
202 second chamber of cartridge 200
203 proximal end of cartridge 200
204 distal end of cartridge 200
205 stop member
207 seal which may comprise a foil seal, bung or similar sealing means
209 feeding channels (outlets) from the cartridge 200
211 securing members
213 base
215 cap
217 channel seals
219 guide notch
221 cap housing
223 cap handle
230 piston
231 housing of piston
233 O-ring
235 proximal end of piston
237 distal end of piston
239 collar
250 alternative embodiment of reservoir for biomaterials; the reservoir being in the form of a cartridge with the chambers each having a generally elongate chamber having a longitudinal axis;
251 Third chamber within the cartridge in the alternative embodiment;
300 mixer
301 proximal end of mixer
302 distal end of mixer
305 Luer lock
307 mixing shaft
309 mixing element
310 alternative mixer
311 inlet channels
313 guide notch
320 alternative mixer
330 alternative mixer
500 cannula
501 proximal end
502 distal end
503 Luer Lock
505 wings
510 partially threaded cannulated screw
512 screw threads for drilling
514 screw threads for assembly
515 fenestration
530 fully threaded cannulated screw
532 screw threads for drilling
534 screw threads for assembly
550 sheath
551 sheath adapter
552 female Luer lock of sheath
553 screw threads
554 distal end of sheath adapter
555 distal end of sheath
556 male Luer lock of sheath adapter
557 threads on sheath adapter
558 internal threads on sheath in ghost outline FIGS. 1 to 3 show different perspective views of a dispenser gun 100 according to one embodiment of the present invention. The dispenser gun 100 comprises a tailored slot 102 for supporting the biomaterial containing cartridge (not shown), while the housing 101 of the system pivotally supports an actuation trigger 103 to advance the plunger drive mechanism. Once the trigger 103 is actuated by drawing it closer to the stationary handle 104, the gripper plate engages with the drive mechanism and this advances the plungers 105, 106. The drive mechanism comprises gripper plate teeth 107 which prevent the plungers 105 and 106 from retracting. The dispenser gun has a release button 108 that allows the surgeon to manually retract the plungers 105, 106 if required in order to remove the cartridge (not shown).

Gripper plate guides 111 and 112 extend vertically from the top of plungers 105 and 106 respectively.

A second slot 109 is further provided on the rear of the plungers 105 and 106. The function of the second slot 109 is to aid with manual retraction of the gripper plate.

Figure 4:
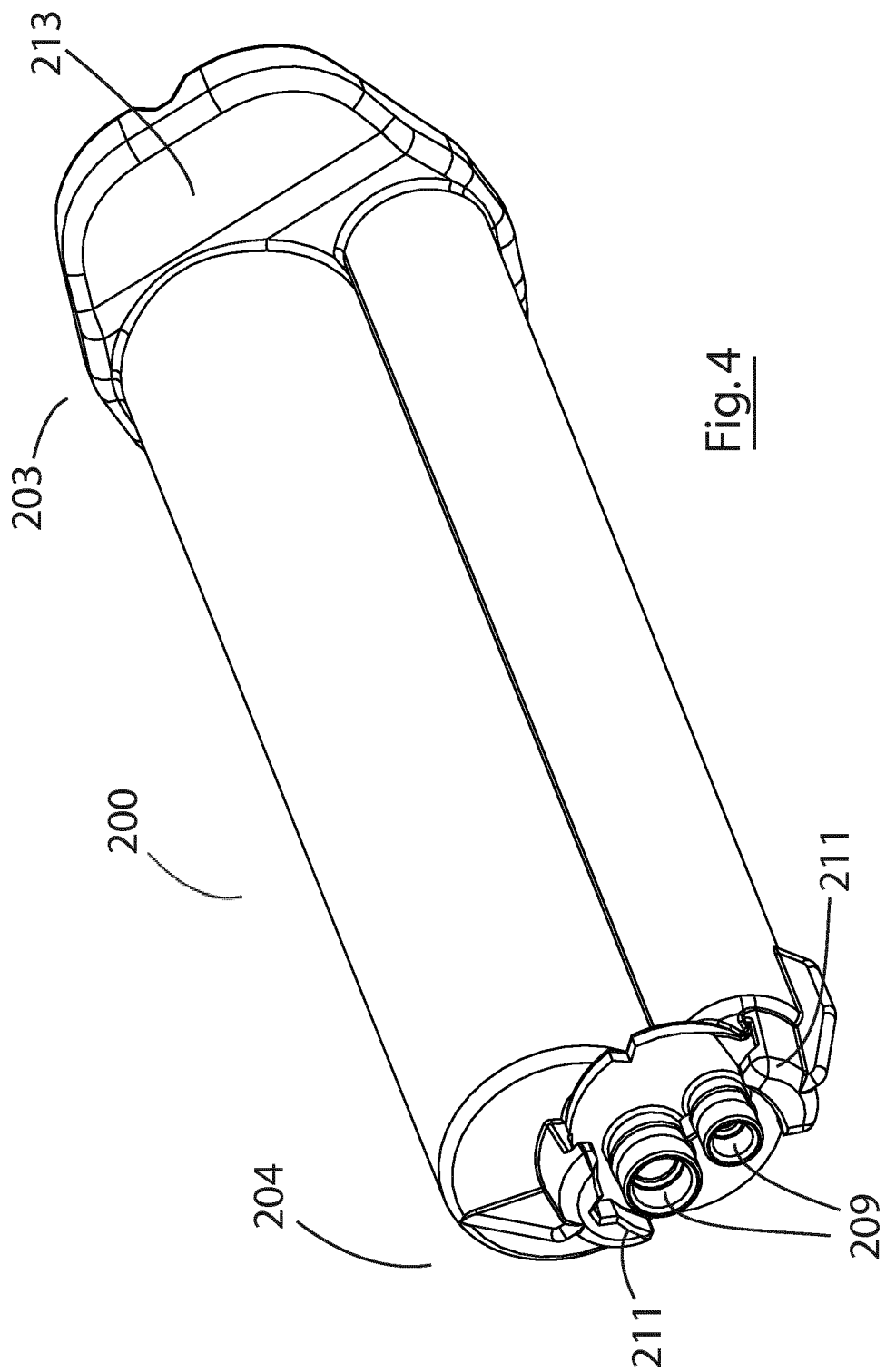
FIG. 4 is a perspective view of a reservoir for sealably containing biomaterial(s); in one embodiment of the present invention, the reservoir comprises a cartridge having the features shown in FIG. 4.
Figure 5:
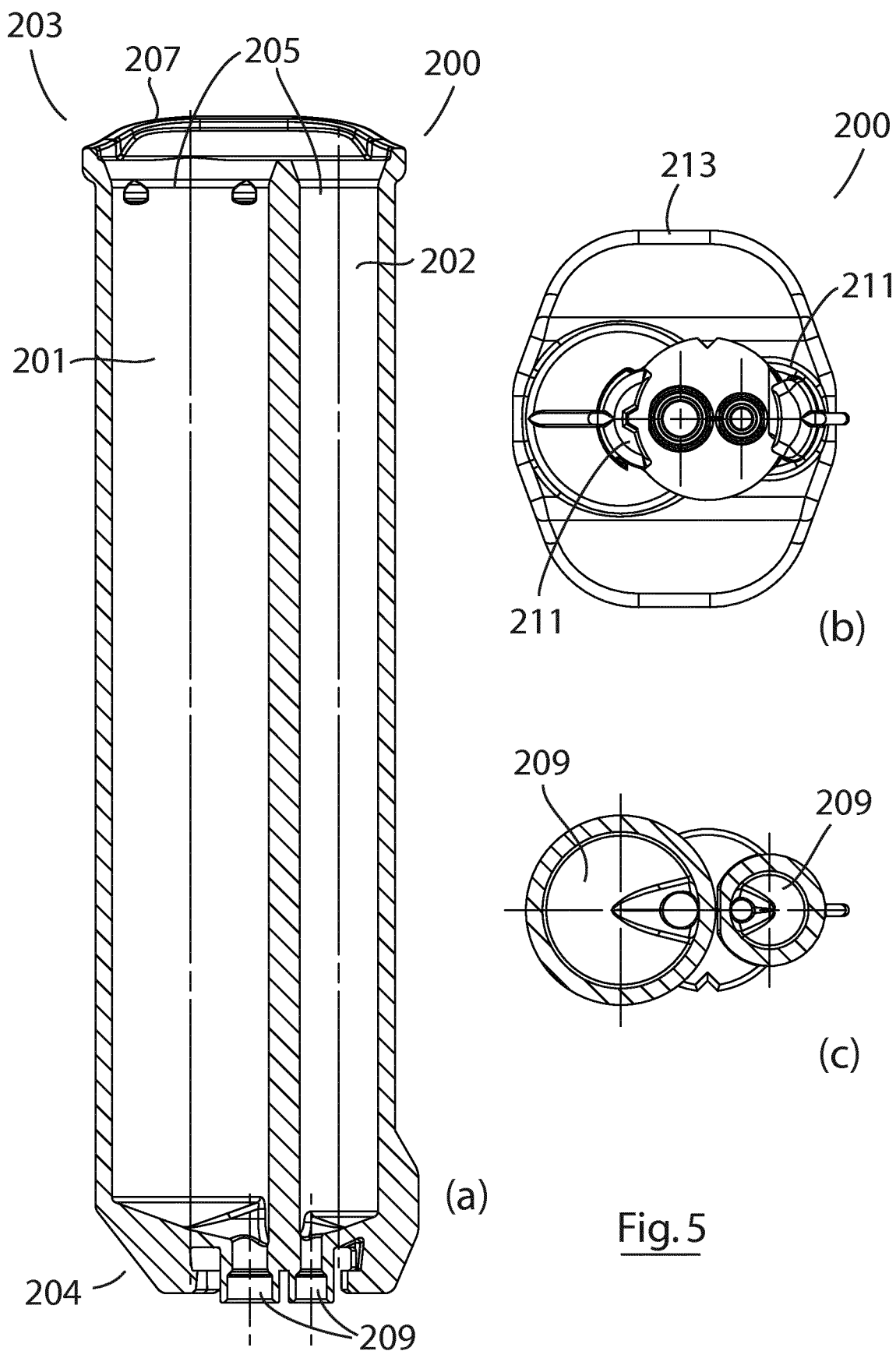
FIG. 5a is a longitudinal sectional view of the cartridge of FIG. 4.
FIG. 5b is a view of the proximal end of the cartridge and FIG. 5c is a cross section of the proximal end of the cartridge showing the feeding channels configured for fluid communication with the mixer device when the cartridge is connected to the mixer device in use.

FIG. 4 is a perspective view of the cartridge in one embodiment, indicated generally by the reference numeral 200. FIG. 5 is a selection of views of a cartridge in one embodiment, indicated generally by reference numeral 200; the views shown in FIG. 5 are, respectively, (a) longitudinal section, (b) a front view and (c) a cross section of the distal end.

The cartridge 200 comprises two chambers 201, 202 providing separate containment of the biomaterial and activator component until it is required at the site of the surgery. Other chambers (not shown) may be added depending on the biomaterial formulation. Each chamber comprises of a longitudinal axis cylinder having proximal end 203 and a distal end 204. All cylinders contain a piston/plunger (detailed in FIGS. 7 and 8), which, are generally positioned at the proximal of the cartridge. A stopping member 205 is located at the proximal end on the cylindrical wall of the cartridge to prevent the piston/plunger from being pushed outside the housing. A foil seal, bung 207 or similar may be fixated at the proximal end 203 of the cartridge to support containment, where the surgeon can remove this seal before usage of the device. The proximal end is further provided with a base configured to be secured in the dispenser gun 100. The distal end 204 of the cartridge contains the feeding channels 209 to mixer. These feeding channels may be covered in a cap 215 (shown in FIG. 6) which is held in place by securing members 211. The number of channels 209 is governed by the number of chambers 201, 202 used. Each of the channels can either be sealed via ultrasonic weld, foil seal, bung cap or similar in order to provide containment before usage. The surgeon will be able to remove this seal manually from the channels in order to expose the contents before placement of the mixer 300 (shown in FIG. 6). All components of the cartridge are manufactured using medical grade polymeric materials that have excellent moisture/oxygen barrier characteristics.

Shown in FIG. 6 is the cartridge cap 215 comprising seals 217 for the channels at the distal end 204 of the cartridge 200 and a guide notch 219 to ensure the correct placement of the cap on the cartridge. The cap is further provided with a handle 221 to aid in the removal of the cap.

Figure 7:
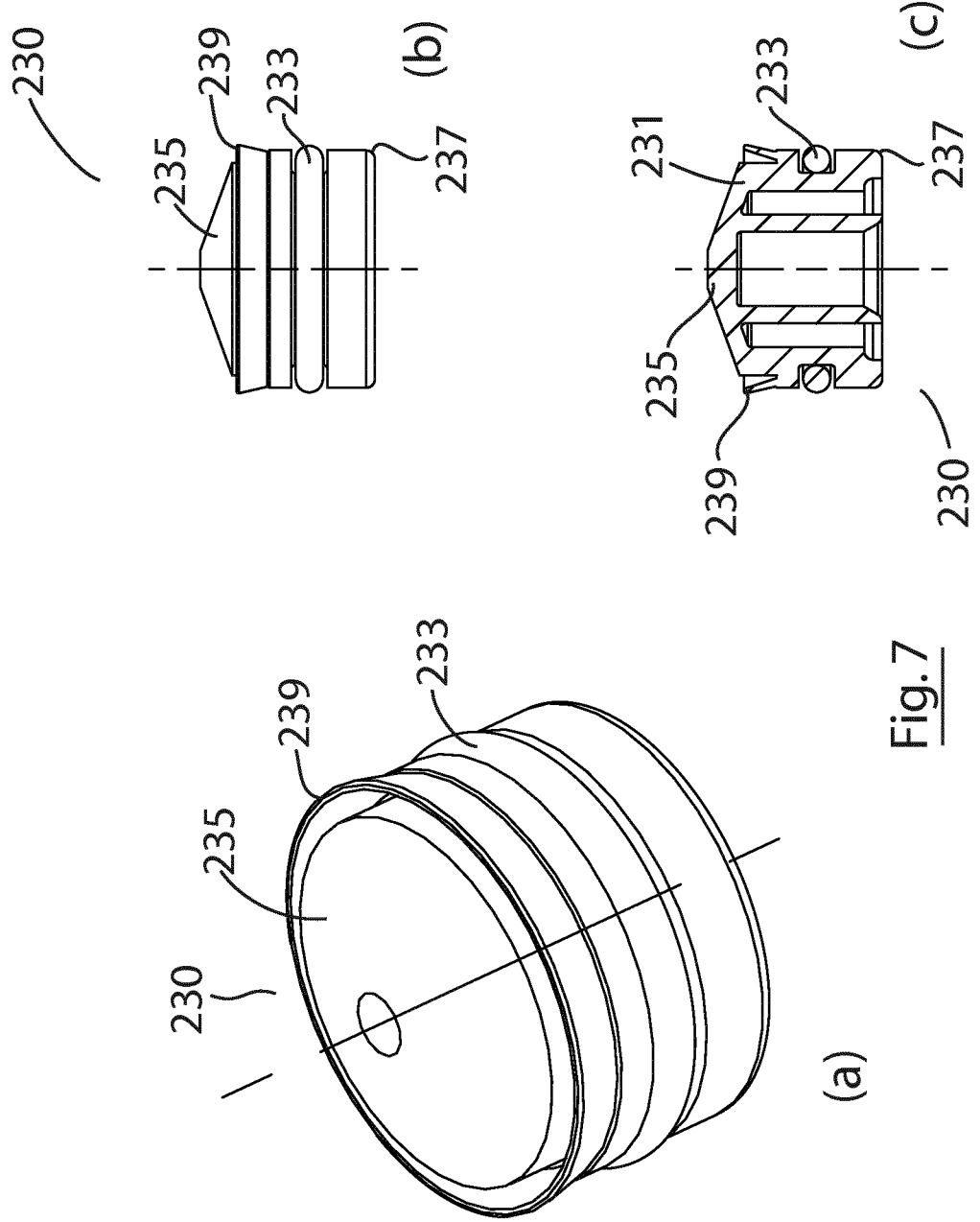

FIG. 7 shows a piston 230 for a cartridge according to the invention. The piston comprises a substantially cylindrical piston housing 231 surrounded by an O-ring(s) 233. The piston has a tapered proximal end 235 and a flat distal end 237. The piston further comprises an outwardly flaring collar 239 on its proximal end which performs the function of a seal.

Figure 8:
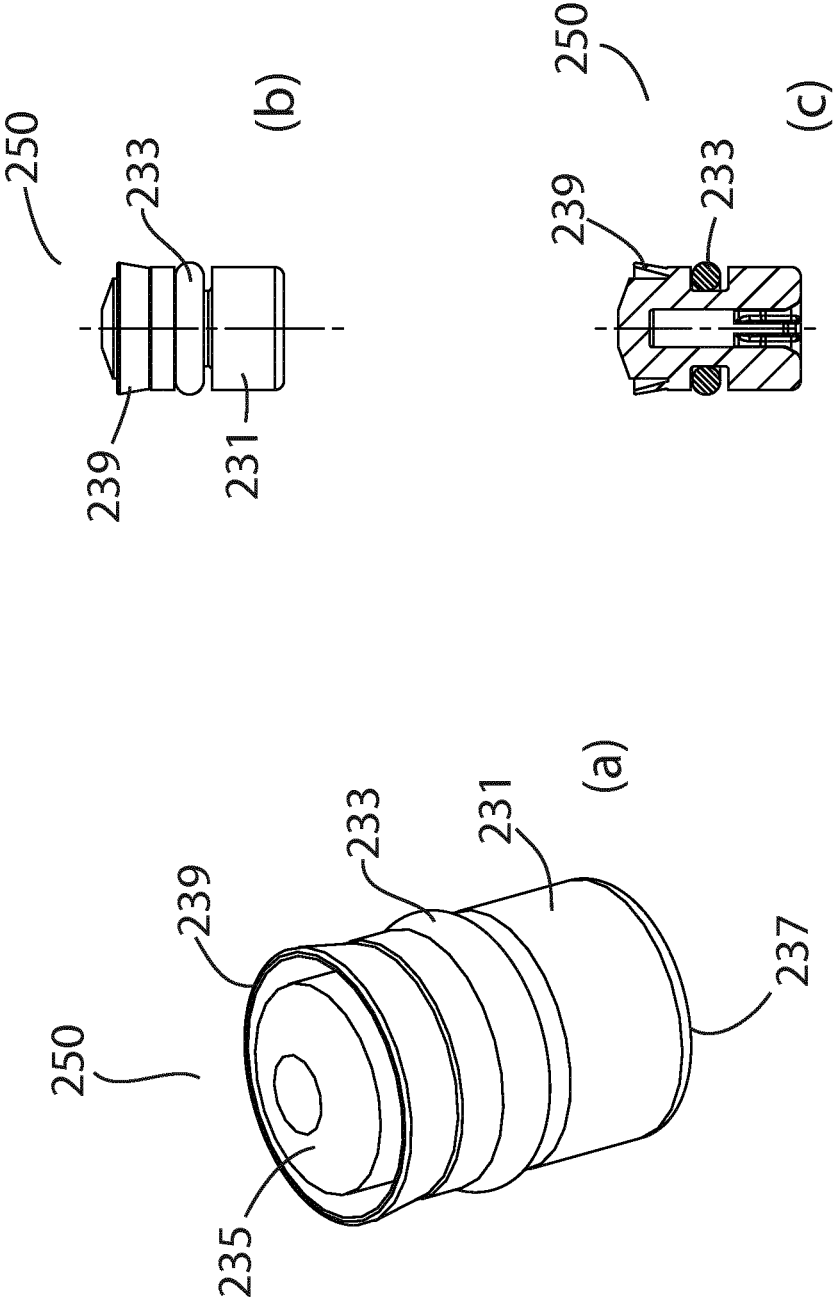

FIG. 8 shows an alternative embodiment of the piston 250 according to the invention. Piston 250 differs from piston 230 primarily in that its height is greater than its diameter. The diameter of piston 230 is greater than the distance from the proximal end to the distal end. This difference results in a different internal construction being required, with the relatively wider piston 230 having a relatively greater amount of empty space internally. This configuration is particularly adept at preventing ingress of water, which may damage the contents of the cartridge.

Figure 9:
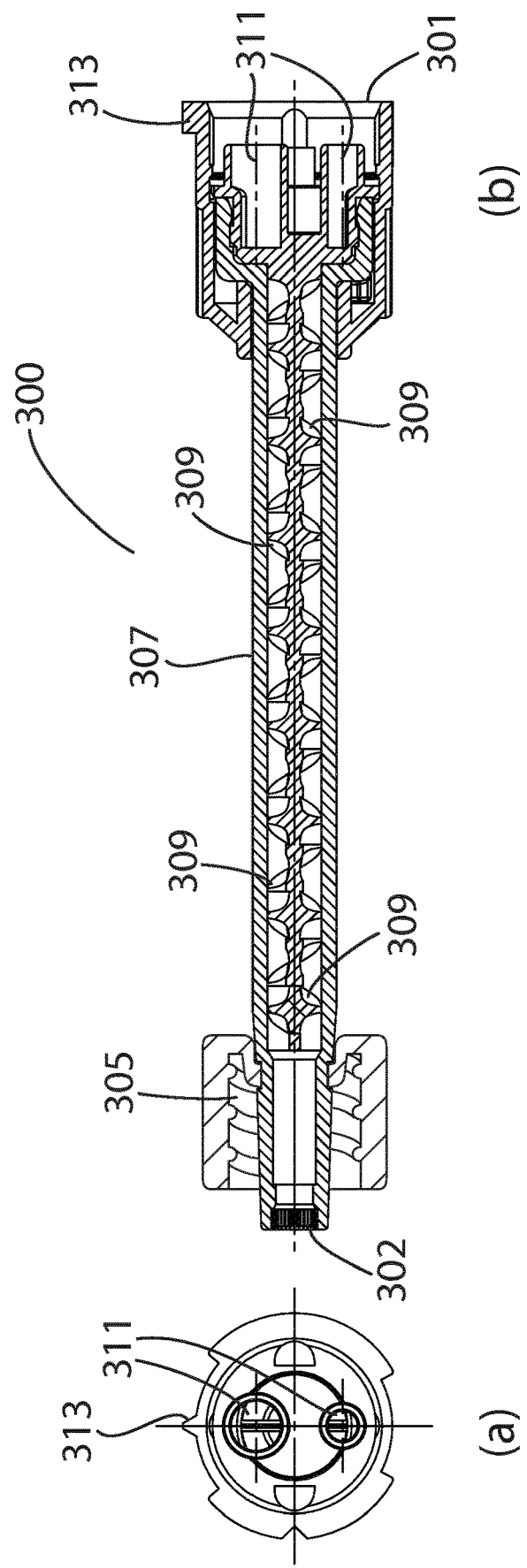

FIG. 9 shows a first embodiment of one embodiment of a mixer 300 according to the present invention.

The mixer 300 comprises a cylindrical shaft having a proximal end 301 and a distal end 302. At the proximal end 301, a specially adapted connector allows the mixer to be attached to a cartridge 200 that contains two or more chambers to support the delivery of the components via the inlet channels 311 to the mixing section. The interface between the cartridge and mixer is design so that a high quality seal is created to prevent loss/leakage of the biomaterials or activator components, having a guide notch 313 to ensure correct connection. At the distal end of the mixer, a Luer lock 305 permits connection of the system to cannulas or other internal fracture fixation devices such as cannulated screws, nails and pins. Between the proximal end 301 and the distal end 302 of the mixer is the mixing section. This section typically comprises helical, baffle or similar mixing elements and these can be provided in multiple configurations to enable handling of different viscosity biomaterials. The biomaterials are mixed by moving them through the mixing shaft 307 where the biomaterial and activator component are brought together. At this stage the curing reaction is initiated, forming the required material at exactly the point of dispensing allowing the user or surgeon to have full control of the setting reaction. Mixing elements may be located throughout the full length of the mixer shaft and may or may not be fixated to the proximal end of the mixer. This configuration (Configuration 1) is typically used for biomaterials that have low viscosities and can mix the components up to 65,500 times. For high viscosity biomaterials, the mixer shaft may contain a smaller number of mixing elements. The mixing elements may be mobile within the mixing shaft or fixed in position.

Figure 10:
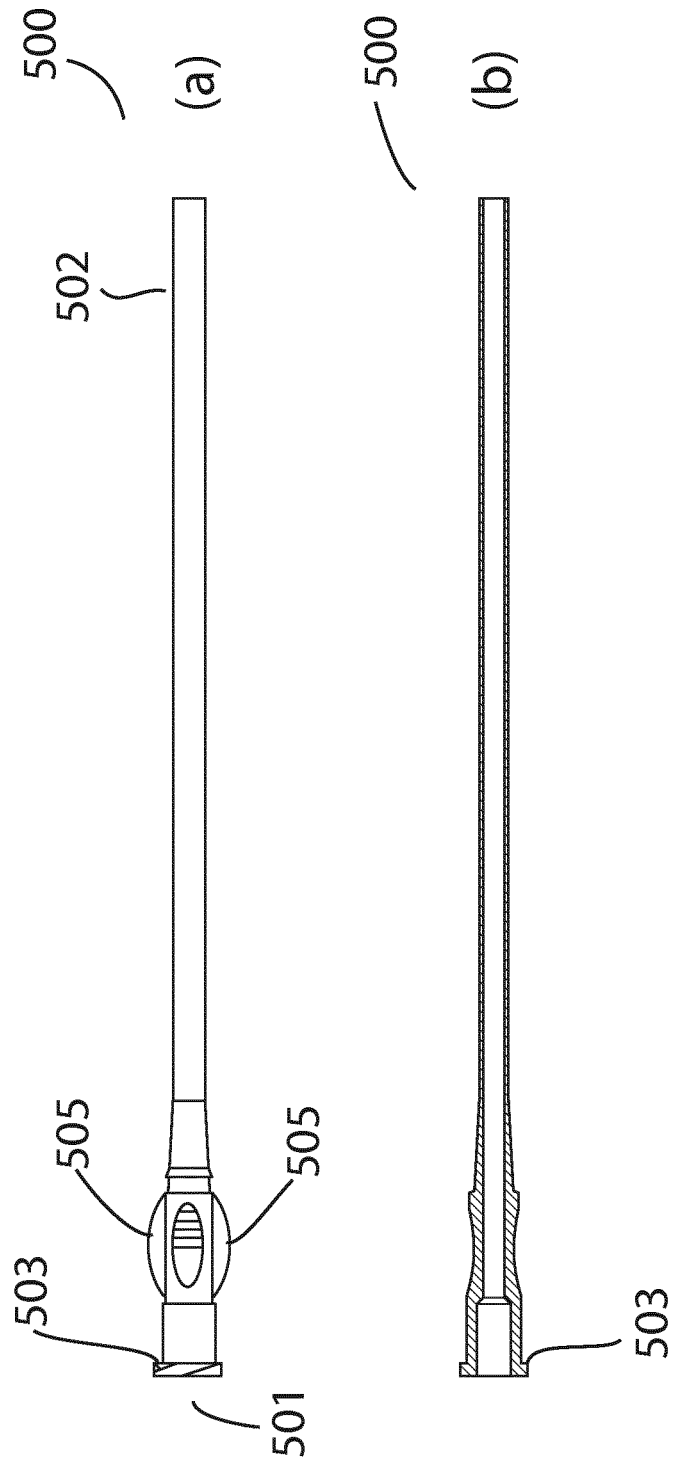

FIG. 10 shows one embodiment of a cannula 500 in accordance with an embodiment of the present invention. The cannula comprises a cylindrical tube having both a proximal end 501 and a distal end 502 with an internal diameter of 2.55 mm and an outer diameter of 3.5 mm. At the proximal end, the cannula has a male Luer lock 503 which can fit securely on to the female Luer lock of the mixer. In addition, this end of the cannula includes two wings 505 to allow the user or surgeon to secure the cannula to the mixer with ease. At the distal end of the cannula, this is where the final mixed biomaterial is dispensed from the complete device into the target area. The distal end can have a round nose tip with an opening of 1.5 mm or a flat tip (as shown in FIG. 10*a*) with an opening of 2.5 mm (diameters may be varied depending on the biomaterial to be dispensed. A flat tip is typically used where the mixing elements are included in the mixer. When there is no mixing elements in the mixer, the mixing elements are typically placed in the cannula. A round nose tip cannula is used in this case to prevent the mixing elements from being forced out of the cannula housing as the biomaterials and activator components are being dispensed. The purpose of moving the mixing elements from the mixer to the distal end of the cannula is to allow the biomaterials and activator components to come together for an extended period of time prior to reaching the elements. This helps to reduce the viscosity by partially mixing the components, therefore; allowing them to flow more freely through the mixing elements. In terms of design, the reduction of the internal diameters from the mixer to the cannula supports the partial mixing process, due to the turbulence created at this section. In addition, the reduction of the internal diameter increases the velocity of the components, thus, reducing the overall pressure in contrast to the alternative systems previously mentioned. A tapered needle tip, a bevelled needle tip or any other needle tip shape may also be used.

One of the principle design features that generates pressure in the previous mentioned systems is the positioning of the mixing elements. By having them positioned at an early stage in the process, this restricts viscosity reduction of the components while creating a flow barrier prior to reaching the reduced internal diameters between the mixer and cannula. This reduces the velocity of the components in the system, therefore; increasing the pressure. The working length of the cannula can vary in size depending on the viscosity of the biomaterial and the surgeon requirements. Having a cannula with a longer working length allows the biomaterial and activator component more time to mix before being dispensed to the target area and this applies for all aforementioned systems. In the system where the mixer contains no mixing elements and the cannula contains mixing elements at the distal end, a longer cannula allows the viscosity of the components to decrease substantially, therefore; enhancing the injectability for the surgeon.

Figure 11:
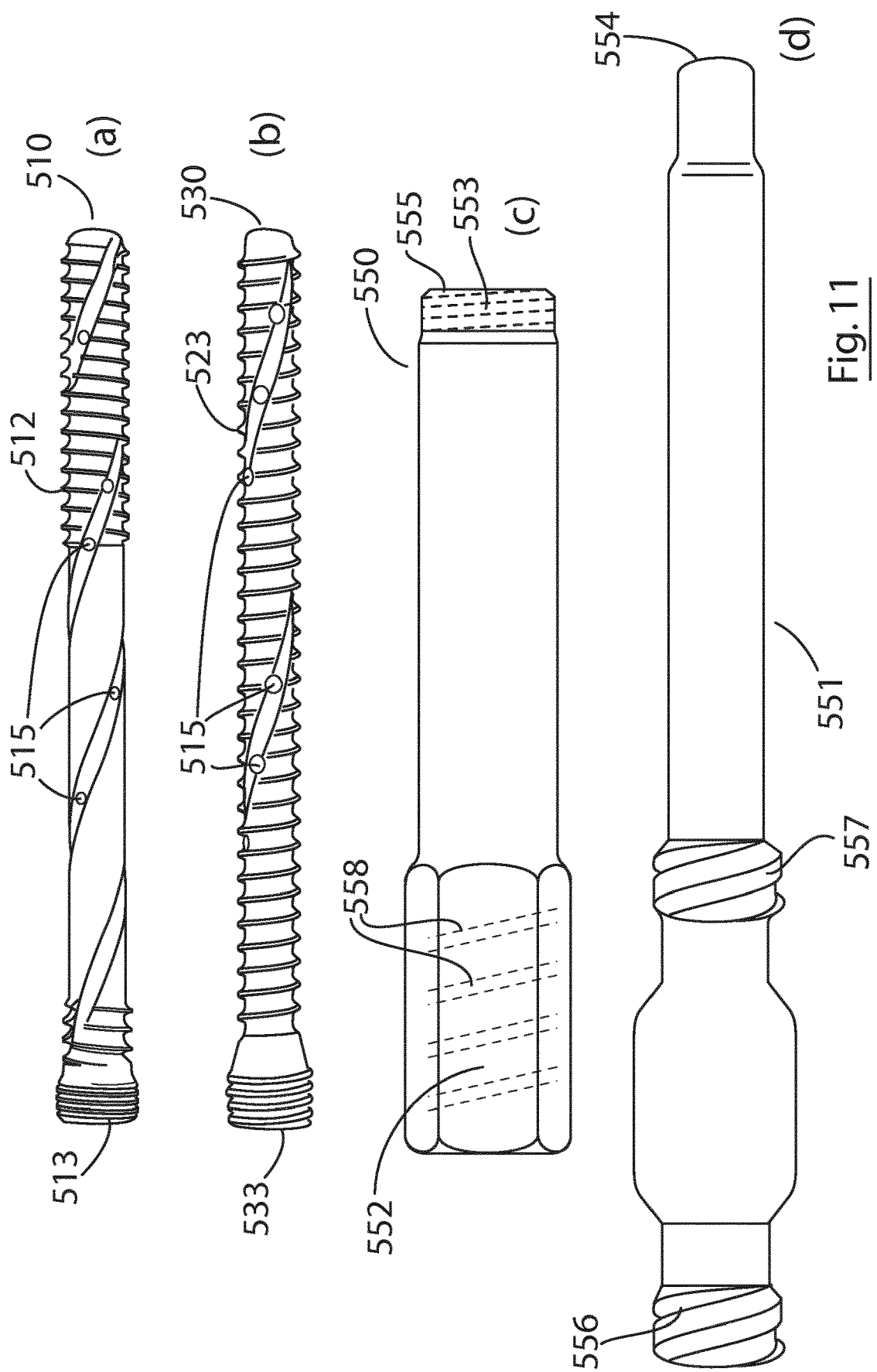
FIG. 11a is a side view of a cannulated fracture fixation device which in this embodiment, is in the form of a partially threaded screw, with the ridges of the screw threads extending only partially along the length of the fracture fixation device.
FIG. 11b is a side view of an alternative embodiment of a cannulated, fracture fixation device which, in this embodiment is in the form of a threaded screw, with the ridges of the screw threads extending substantially along the entire length of the fracture fixation device.
FIG. 11c is a side view of a sheath according to the invention, for engaging with a fracture fixation device.
FIG. 11(d) is a side view of a sheath adapter according to the invention, the sheath adapter being configured to be accommodated within the sheath of FIG. 11c.
FIG. 11(e) is a side view of the sheath adapter partially inserted into the sheath.
FIG. 11(f) is a side view of the sheath adapter fully inserted in the sheath with the distal end of the sheath adapter protruding beyond the distal end of the sheath and the sheath having screw threaded arrangement on the internal face of the distal end thereof for engaging with a fracture fixation device.

FIG. 11 shows a variety of internal fracture fixation devices, in this instance cannulated screws 510, 530 that can be coupled to any of the mixers of the invention by the use of a sheath 550 and sheath adaptor 551 (provided with the internal fracture fixation device). Screws 510 and 530 are cannulated and may have fenestrations 515, though which biomaterial may pass when the screw 510, 550 is in place in the bone. The biomaterial passing out through the fenestrations in the screws acts as a bond between the screw and the bone. This is a more secure fit than the result of a screw being fixed in place in the bone merely by its threads. Indeed, it means that the screw does not need to be fully threaded for a secure fit. The screw may have a threaded distal end, and a smooth middle and proximal end, with fenestrations along the full length to allow the biomaterial to exit through the fenestrations and form a seal between the bone and the screw along the full length of the screw. This is advantageous as the drilling action of the threads on the bone may be undesirable as it may cause small fractures in the surrounding bone. The locations of the fenestrations also allow more viscous biomaterials to pass through the screw than would otherwise be possible. At the distal end 554 of the sheath adapter is a standard screwing thread 553 (not shown) that allows the surgeon to fasten the sheath adapter onto the internal fracture fixation device by screwing in a clockwise direction. Complementary screw threads 513, 533 are provided on the cannulated screw 510, 530. At the proximal end of the sheath is a female Luer lock 552 that permits connection of the sheath to the sheath adaptor. The distal end of the sheath adaptor 554 is placed inside the proximal end of the sheath. When the sheath adaptor is fastened in place by screwing in a clockwise direction, the distal end of the device protrudes past the distal end of the sheath 555 and into the cannula opening of the proximal end of the internal fracture fixation device. At the proximal end of the sheath adaptor, a male Luer lock 556 is provided that allows the overall device (sheath 550, sheath adaptor 551 and internal fracture fixation device 510, 530) to be connected to any of the mixers in Configurations 1-4 as shown in FIGS. 12 to 15.

FIGS. 12 to 15 show configurations 1 to 4 respectively of the cannulas for bone void filling or to multiple internal fracture fixation devices for augmented fixation trauma indications (i.e. to be used without the cannula component).

With the mixer 300, 310, 320 in configurations 1-3, mixing of the biomaterials with the activator components is completed prior to entering the sheath adaptor and internal fracture fixation device.

Figure 12:
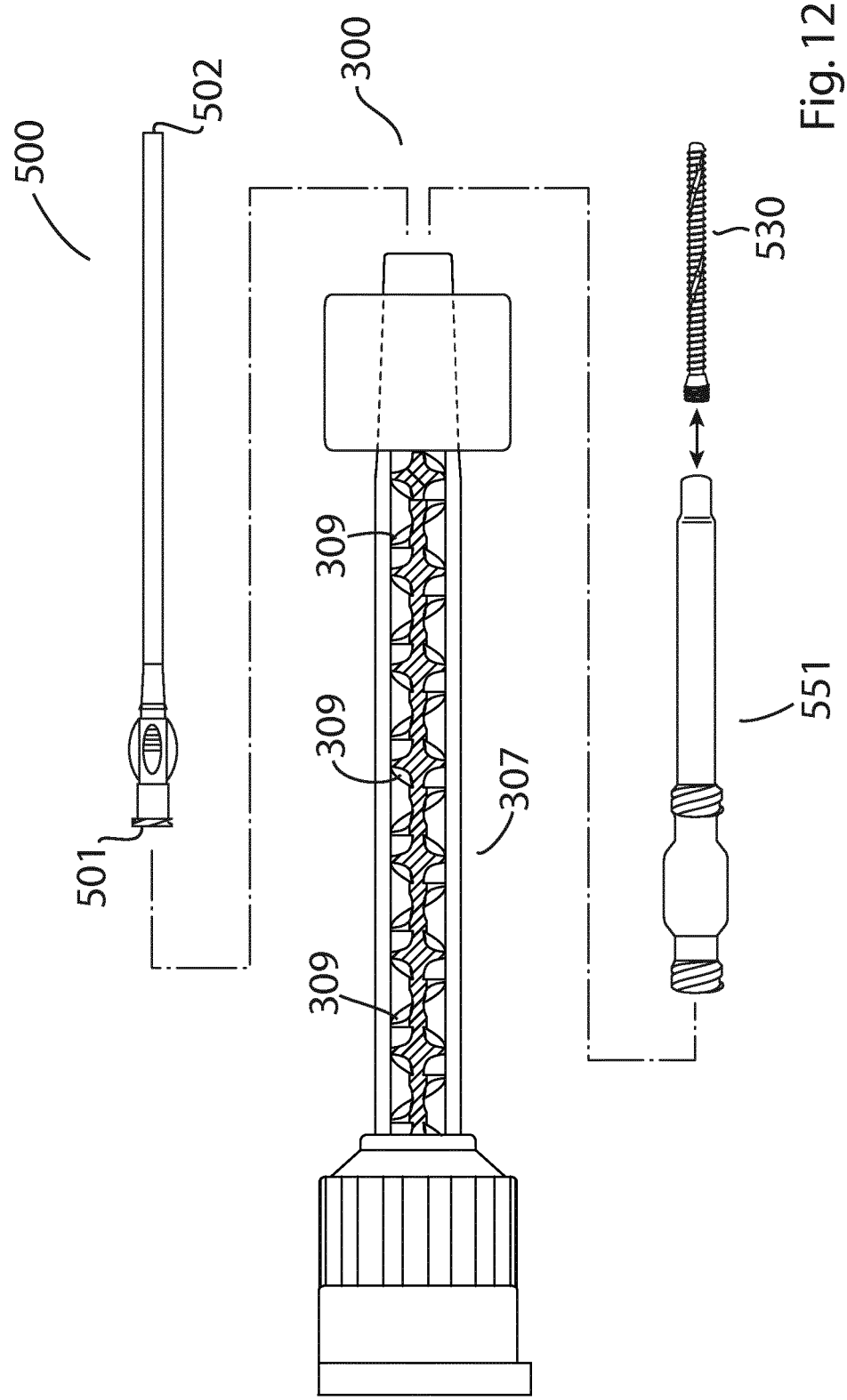
FIG. 12 is a schematic view of a first configuration of a system of the present invention comprising the mixer device of FIG. 9, the sheath of FIG. 11c, the sheath adapter, a cannula and an internal fracture fixation device according to the invention.

FIG. 12 shows a first configuration of a mixer 300, cannula 500, sheath 550, sheath adapter 551 and screw 530 ensemble in accordance with the invention. The mixing elements 309 are fixated at the proximal end of the mixer and extend up the full length of the mixing shaft 307. This arrangement (Configuration 1) is typically used for biomaterials that have low viscosities and delivery device in this embodiment, can mix the components up to 65,500 times owing to the large number of mixing elements.

Figure 13:
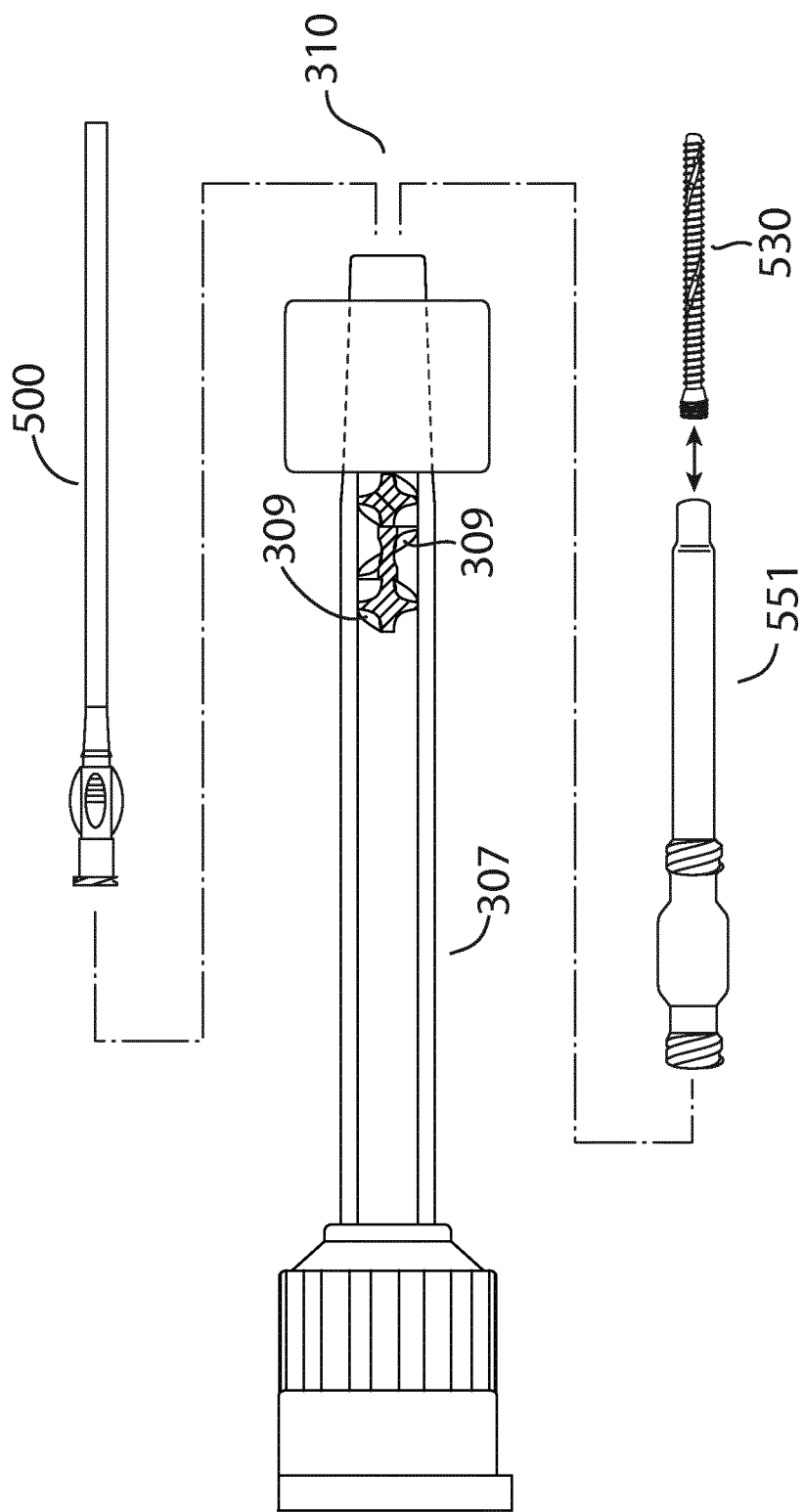
FIG. 13 is a schematic view of a second configuration of a system of the present invention comprising a mixer, a sheath, a sheath adapter, a cannula and an internal fracture fixation device according to the invention.

FIG. 13 shows a second configuration of a mixer 310, cannula 500, sheath 550 and screw 530 ensemble in accordance with the invention. A small number of mixing elements 309 are mobile along the full length of the mixing shaft 307. This configuration is typically used for high viscosity biomaterials. In an alternative embodiment, the mixing elements may be arranged such that they are not fixed but are free to move along the full length of the mixer shaft or substantially the full length of the mixer shaft. In a further alternative embodiment, the mixing elements may be fixated to the proximal end of the mixer shaft. When high viscosity biomaterials and activator components are dispensed into the mixer shaft 307 containing the mobile mixing elements, the biomaterials and activator components have time to partly mix before being pressurized against the mixing elements at the distal end, which completes the mixing process. This helps to reduce the viscosity of the components, therefore, allowing them to flow more freely through the mixing elements 309. By doing so, the injectability force is reduced significantly, thus, enhancing the usability of the device.

Figure 14:
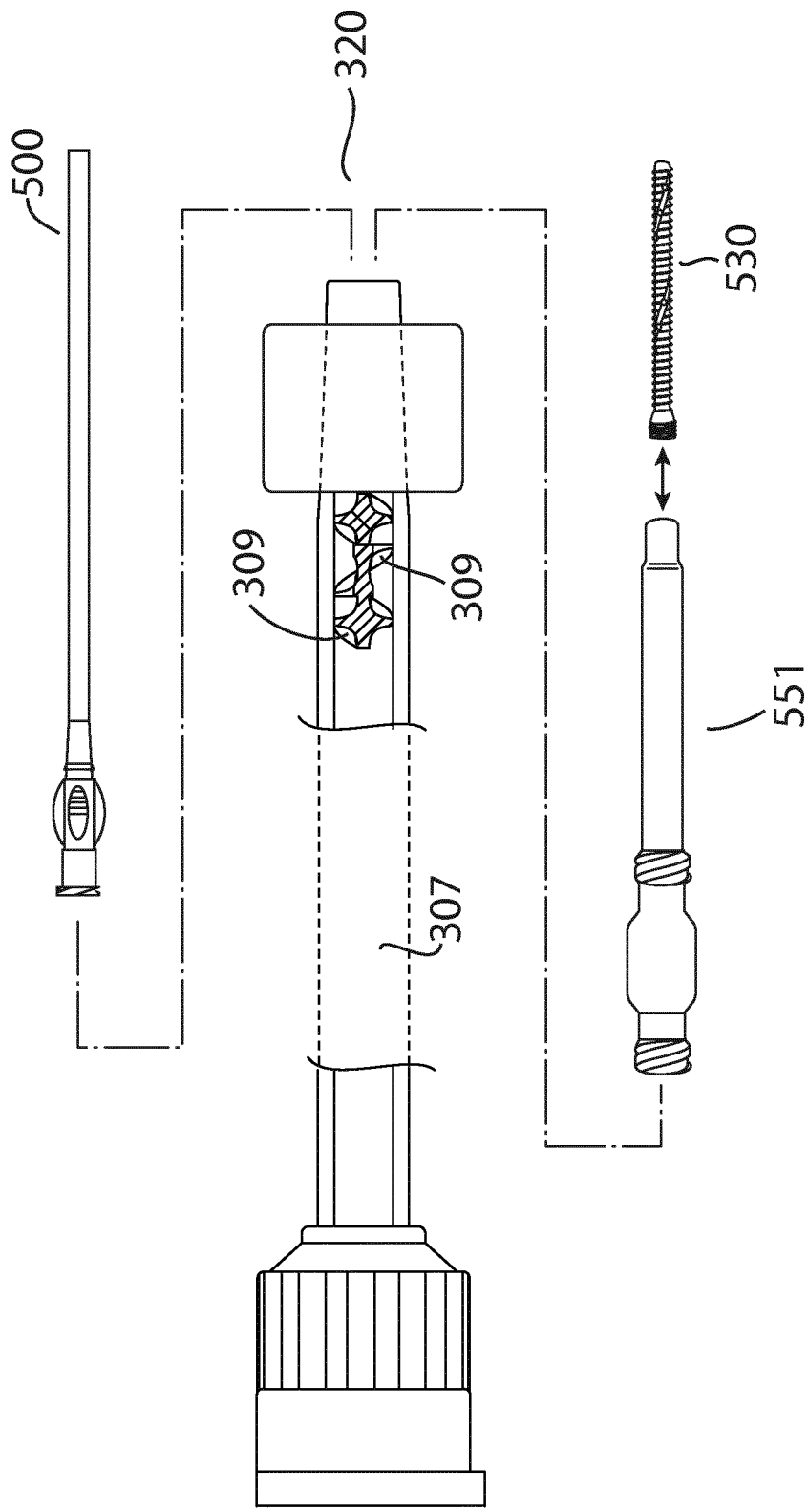
FIG. 14 is a schematic view of a third configuration of a system of the present invention comprising a mixer, a sheath, a sheath adapter, a cannula and an internal fracture fixation device according to the invention.

FIG. 14 depicts a third configuration having an alternative mixer 320. This configuration is a delivery device for high viscosity biomaterials comprising a small number of mobile mixing elements 309 in an extended mixer shaft 307. Once the components enter the mixing shaft 307 from the cartridge 200, they have additional time to partly mix before reaching the mixing elements 309 at the distal end. This helps to reduce the viscosity of the components further, allowing them to flow more freely through the mixing elements.

Figure 15:
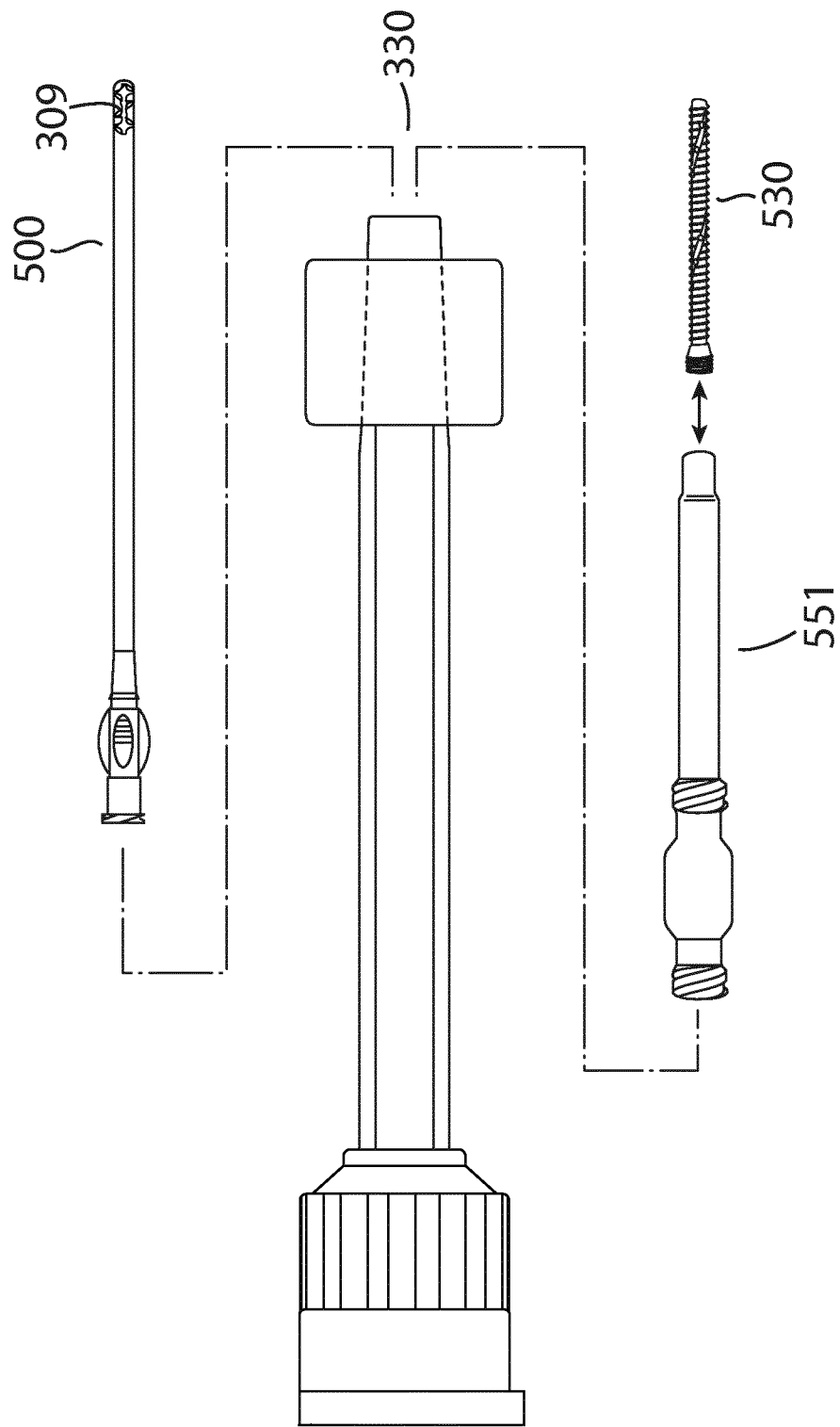
FIG. 15 is a schematic view of a fourth configuration of a mixer, a sheath, a sheath adapter, a cannula and an internal fracture fixation device according to the invention.

FIG. 15 shows a fourth configuration in which the mixing shaft contains no mixing elements. This is particularly suited to high viscosity biomaterial. There are mixing elements 309 in the distal end of the cannula which is sufficient to produce a homogenous mixture on dispensation.

For the mixer 330 in Configuration 4, the biomaterials and activator components are mixed to completion upon entering the internal fracture fixation device. In this design, the complete mixing process is further in the system as the components travel through the various contours of the sheath adaptor and the cannulated internal fracture fixation device. These contours create sufficient turbulence to homogeneously mix the components to provide the required setting time and compressive strength characteristics.

In this embodiment, the components are mixed at a later stage, such as in the cannula device 500 or other internal fracture fixation devices such as cannulated screws, nails and pins. By removing the mixing elements entirely from the mixer, this allows the biomaterial and activator components to partly but sufficiently mix and reduce their viscosities before exiting the mixer. The cannula is comprised of a cylindrical tube having both proximal and distal ends with an internal diameter of 2.55 mm and an outer diameter of 3.5 mm (or as otherwise specified by the biomaterial to be implanted). At the proximal end, the cannula has a male Luer lock which can fit securely on to the female Luer lock of the mixer. In addition, this end of the cannula includes two wings to allow the surgeon to secure the cannula to the mixer with ease. At the distal end of the cannula, this is where the final mixed biomaterial is dispensed from the complete device into the target area. The distal end can have a round nose tip with an opening of 1.5 mm or a flat tip with an opening of 2.5 mm (or as otherwise specified by the biomaterial to be implanted). A flat tip is typically used where the mixing elements are included in the mixer. When there are no mixing elements in the mixer, the mixing elements are typically placed in the cannula. A round nose tip cannula is used in this case to prevent the mixing elements from being moved out of the cannula housing as the biomaterials and activator components are being dispensed. The purpose of moving the mixing elements 309 from the mixer to the distal end of the cannula is to allow the biomaterials and activator components to come together for an extended period of time prior to reaching the elements. This helps to reduce the viscosity by partially mixing the components, therefore; allowing them to flow more freely through the mixing elements. In terms of design, the reduction of the internal diameters from the mixer to the cannula supports the partial mixing process, due to the turbulence created at this section. In addition, the reduction of the internal diameter increases the velocity of the components, thus, reducing the overall pressure in contrast to the alternative systems previously mentioned. One of the principle design features that generates pressure in the previous mentioned systems is the positioning of the mixing elements. By having them positioned at an early stage in the process, this restricts viscosity reduction of the components while creating a flow barrier prior to reaching the reduced internal diameters between the mixer and cannula. This reduces the velocity of the components in the system, therefore; increasing the pressure. The working length of the cannula can vary in size depending on the viscosity of the biomaterial and the surgeon requirements. Having a cannula with a longer working length allows the biomaterial and activator component more time to mix before being dispensed to the target area and this applies for all aforementioned systems. In the system where the mixer contains no mixing elements and the cannula contains mixing elements at the distal end, a longer cannula allows the viscosity of the components to decrease substantially, therefore; enhancing the injectability for the surgeon.

The surgeon has the option to connect the mixers of Configurations 1-4 to the cannulas for bone void filling or to multiple internal fracture fixation devices for augmented fixation trauma indications (i.e. to be used without the cannula component). A detailed explanation was already provided for the overall functionality of the cannula option. For the internal fracture fixation devices such as screws, pins, nails or similar, they have the ability to be connected to each mixer configurations by the use of a sheath and sheath adaptor (provided with the internal fracture fixation device). At the distal end of the sheath is a standard screwing thread that allows the surgeon to fasten the sheath onto the internal fracture fixation device by screwing in a clockwise direction. At the proximal end of the sheath is a female Luer lock that permits connection of the sheath to the sheath adaptor. The distal end of the sheath adaptor is placed inside the proximal end of the sheath. When the sheath adaptor is fastened in place by screwing in a clockwise direction, the distal end of the device protrudes past the distal end of the sheath and into the cannula opening of the proximal end of the internal fracture fixation device. At the proximal end of the sheath adaptor is a male Luer lock that allows the overall device (sheath, sheath adaptor and internal fracture fixation device) to be connected to any of the mixers in configurations 1-4. With the mixer in configurations 1-3, mixing of the biomaterials with the activator components is completed prior to entering the sheath adaptor and internal fracture fixation device. For the mixer in Configuration 4, the biomaterials and activator components are mixed to completion upon entering the internal fracture fixation device. In this design, the complete mixing process is further in the system as the components travel through the various contours of the sheath adaptor and the cannulated internal fracture fixation device. These contours create sufficient turbulence to homogeneously mix the components to provide the required setting time and compressive strength characteristics.

Figure 16:
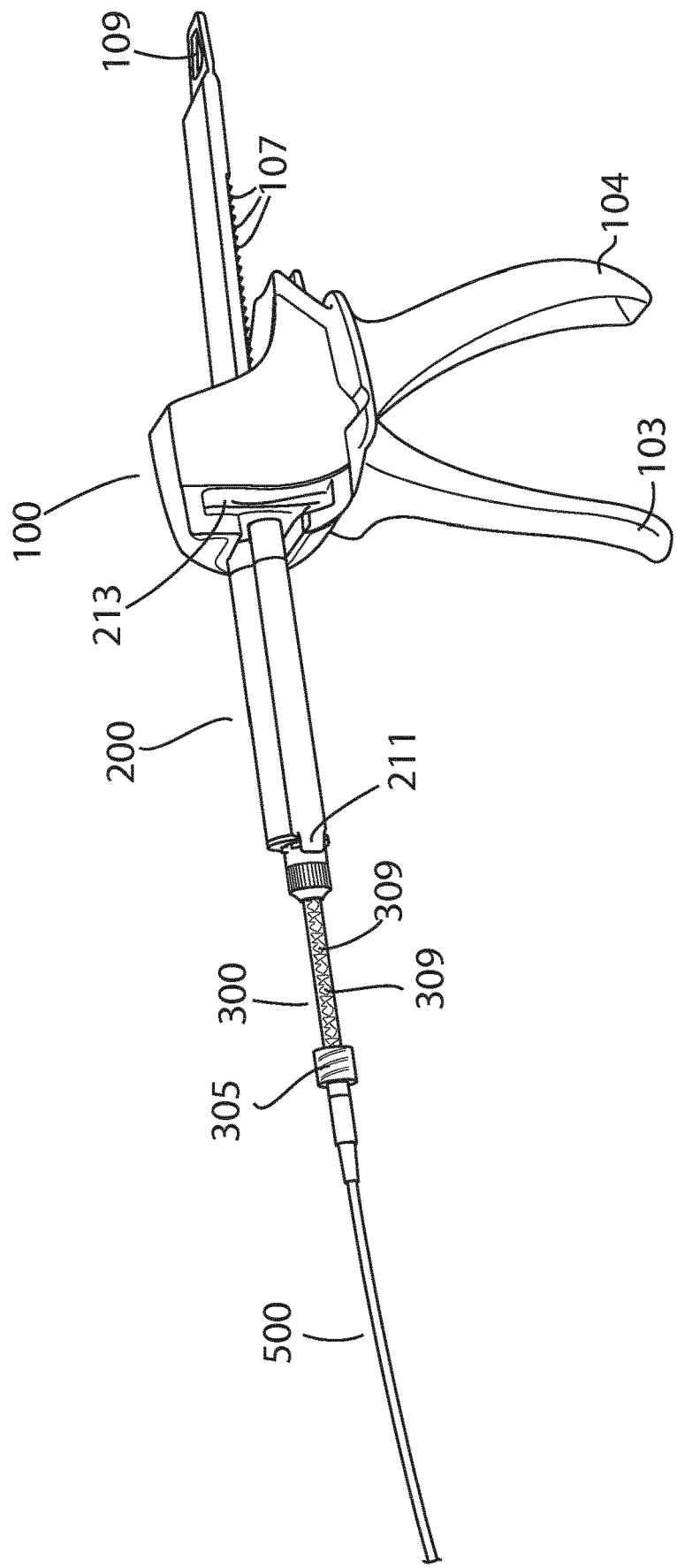
FIG. 16 is a perspective view of a fully assembled embodiment of the invention.

One fully assembled configuration having a cannula is shown in FIG. 16.

In use the cannula 500 is fastened onto the mixer 300 by a Luer lock 305.

The parts can be assembled very quickly within the operating theatre at any point prior to use of the system. The biomaterial fracture fixation system is a 'point and shoot' set-up, simply attach the mixer and cannula and squeeze the trigger on the dispenser gun for simple delivery at the target site. The system also permits a "stop-start" feature. Once injection has stopped, injection may recommence within a short period without mixer exchange or up to 2 hours later by removing the used mixer and replacing it with a fresh one.

This system is capable of delivering any required biomaterial, provided it is formulated to permit flow through the mixer and cannula systems. The dispenser gun 100 provides a significant mechanical advantage to the surgeon, providing 5.5× the force to the cartridge over that which the surgeon puts on the dispenser gun 100. This allows the surgeon to inject biomaterials in a manner that is not possible using more traditional systems.

Figure 17:
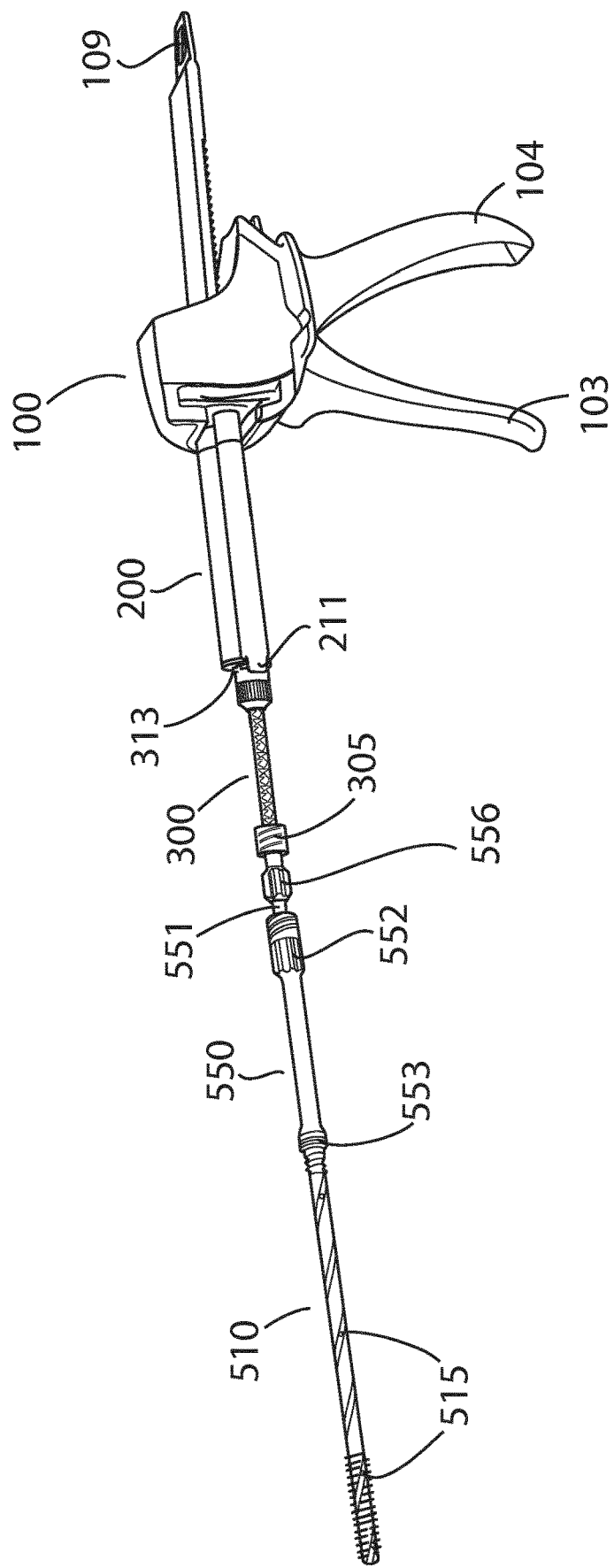
FIG. 17 is a perspective view of an alternative embodiment of the invention.

FIG. 17 is an alternative assembled delivery system.

In use the proximal end of the screw 510 is fastened onto the distal end of the sheath adapter 551. The proximal end of the sheath adapter 551 is connected to the distal end of the mixer 300 by Luer lock 305.

The four parts can be assembled very quickly within the operating theatre at any point prior to use of the system. The biomaterial fracture fixation system is a 'point and shoot' set-up, whereby the mixer is attached in one step and, if required, a cannula, the trigger is squeezed on the dispenser gun for simple delivery at the target site. The system also permits a "stop-start" feature. Once injection has stopped, injection may recommence within a short period (30 seconds) without mixer exchange or up to 2 hours later by removing the used mixer and replacing it with a fresh one.

This system is capable of delivering any required biomaterial, provided it is formulated to permit flow through the mixer and cannula systems. The dispenser gun provides a significant mechanical advantage to the surgeon, providing 5.5× the force to the cartridge over that which the surgeon puts on the dispenser gun. This allows the surgeon to inject biomaterials in a manner that is not possible using more traditional systems.

This system comprises a fenestrated screw 510. Once the screw is in place in a bone as an internal fixation device, the biomaterial may pass through the holes or fenestrations 515 in the screw and out the distal end. This creates a stronger bond between the bone and the screw than if just the bone and screw were present. The positioning of the fenestrations also helps highly viscous biomaterial travel through the screw to the distal end.

The method of delivery of biomaterial to a desired site, in accordance with the present invention, will now be described:

The method of delivering biomaterial to a desired site using the biomaterial delivery system involves the following steps:

Assembling the biomaterial delivery system by carrying out the following steps:
 1. Attaching the cartridge (with two or more chambers) to the dispenser gun;
 2. Attaching the mixer (with Luer or similar lock fitting) to the cartridge; and
 3. Attaching the cannula or internal fracture fixation devices (screws, nails and pins) to the mixer.

Following this assembly, the cement can be delivered by actuating the device where typically, the actuator comprises an actuator trigger operable by hand, so that typically, by squeezing the trigger to actuate the delivery device, the biomaterial and activation component(s) pass through the mixer and cannula (if required), initiating the curing reaction.

All embodiments/configurations of the mixing system allow the components to mix several times before targeted delivery to ensure the desirable performance criteria have been met.

The dispenser gun of the present invention is designed to allow ease of positioning of the cartridge without any excessive force or difficulty on the part of the surgeon. In using the dispenser gun, the force experienced by the surgeon is 5.5 times less than the force being applied to the cartridge. The mean force required to extrude cement through the configuration 1 mixing system (design with largest force) is approximately 400 N, which is reduced to 72.7 N applied by the operator of the dispenser gun. This is notably below the force calculated to be achievable by >95% of women according to the Human Factors Engineering Standard (ANSI/AAMI HE75, 2009).

Testing on this system has shown the following:
 The cartridge-mixer seal will tolerate forces up to 800 N before leakage occurs.
 The cartridge will tolerate internal forces of up to 1200 N before breaking.
 After initial injection through the mixer/cannula, restarting injection may occur up to 30 seconds later without requiring a change of mixer/cannula.
 Hours after the initial injection, it is possible to restart injection by removing the mixer/cannula and placing a new one on the cartridge.
 For biomaterials that cannot be injected though the Configuration 1 system (surpasses threshold of 700 N) due to formulation, the biomaterial can be easily injected through the Configuration 4 system (mean injection force of 270 N)—see FIG. 19.
 Biomaterial expiry (shelf life) is maximized while using the Configuration 2, 3 and 4 systems. Specifically, one of the factors which determines the expiration of a biomaterial is the time period it takes the injectability force to surpass a threshold of 700 N.
 Complete mixing of the biomaterial with the activator component is indicated by Wet Field Set Penetration. Results for configurations 1, 2 and 4 demonstrate that a value of 8 MPa (specified value for the biomaterial tested) was reached within the threshold of 10 minutes, using the same biomaterial over different material ages.

The biomaterial used for the aforementioned testing has a shelf life of 3 months when delivered through Configuration 1. Configuration 1 is unable to dispense the plus 4-month shelf life biomaterial due to an increase in viscosity of an already high viscosity material over time. Configuration 2 and 4 are able to dispense the expired biomaterial with ease and provide a homogeneous mixture (biomaterial and activator component) that ensures the acceptance criteria for each of the essential characteristics are achieved i.e. Injectability Force, Compressive Strength and Wet Field Set Penetration.

Figure 19:
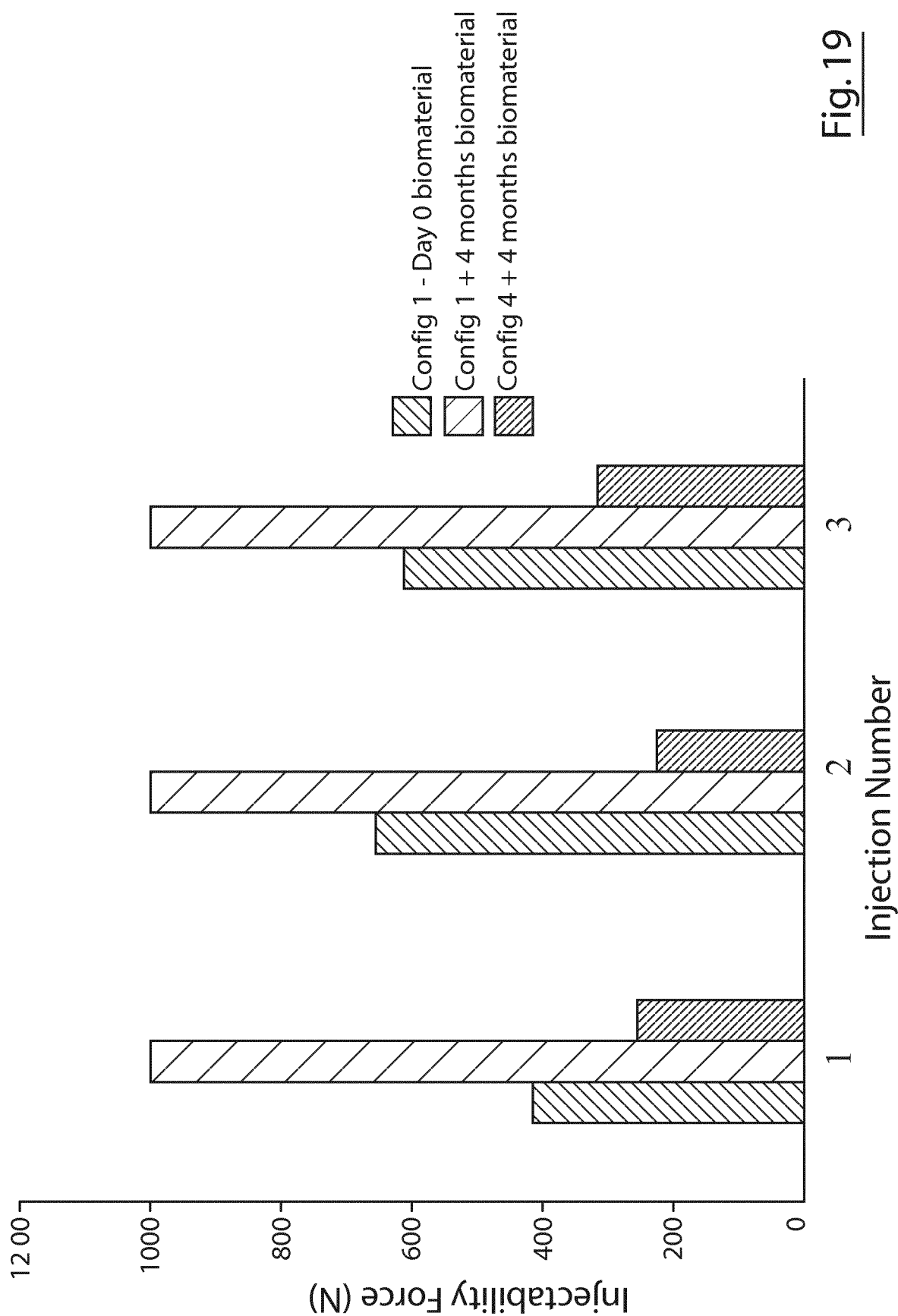
FIG. 19 is bar chart depicting a comparison of the Injectability Force for the system in the first configuration (Configuration 1) system with a new biomaterial (0 days old) and an expired biomaterial (+4 months old). Comparison of Configuration 1 and Configuration 4 systems using an expired biomaterial (+4 months old) only.

FIG. 19 is a comparison of the Injectability Force for Configuration 1 system with a new biomaterial (0 days old) and an expired biomaterial (+4 months old). Comparison of Configuration 1 and Configuration 4 systems using an expired biomaterial (+4 months old) only.

Table 1: Illustrates that all configurations tested with Wet Field Set Penetration achieved a value of 8 MPa within the 10 min threshold using the same biomaterial over different time periods:

TABLE 1

| | Shelf life time | | | | | |
|---|---|---|---|---|---|---|
| | Day 0 | +4 months | +4 months | +4 months | +4 months | +4 months |
| Configuration | Config. 1 using 16 mixing elements in mixer | Config. 2 using 4 mixing elements in mixer | Config. 2 using 3 mixing elements in mixer | Config. 4 using 16 mixing elements in cannula | Config. 4 using 4 mixing elements in cannula | Config. 4 using cannulated screw |
| Results (minutes) | 7.4 | 7.5 | 7 | 9 | 9.5 | 8 |
| Threshold (minutes) | 10 | 10 | 10 | 10 | 10 | 10 |

As an alternative to the cannula, the mixer (any configuration) may be connected to any internal fracture fixation hardware with a Luer (or similar) connection (e.g. cannulated screws, nails or pins). This grants the surgeon the ability to easily use this system in conjunction with any compatible system to enhance the effect of both.

This system is not restricted to delivering one type of biomaterial. Any biomaterial that is formulated for delivery through the mixer and cannula may be compatible with the delivery system and device of the present invention. The system and device of the present invention also allows the surgeon to deliver multiple types of biomaterials within the one operation. The cartridges containing the required biomaterials are loaded in the dispenser gun as required and delivered as required during surgery to augment the fracture fixation. For example, this allows the surgeon to deliver a high strength slow remodeling cement in areas where stability is important, a high strength load bearing material where fixation is required or an adhesive material where fracture reduction and placement is important.

The advantages of the system, device and method of the present invention include the following:
1. The biomaterial fracture fixation augmentation device is a "point and shoot" medical device related system, allowing simple assembly and controlled delivery of a biomaterial or multiple types of biomaterials by the surgeon during orthopedic and trauma surgery.
2. The biomaterial fracture fixation augmentation device permits a "stop-start" method of delivery. The biomaterial will only start setting once the device trigger is depressed and the biomaterial is delivered in to the mixer and on to the target clinical site. After some material has been delivered, injection may recommence within a short time frame (e.g. 30 seconds) without mixer exchange or up to 2 hours later by replacing the old mixer with a new one.
3. This system is capable of delivering any biomaterial that is compatible with it, i.e. any biomaterial that is formulated to pass through the mixer and/or cannula.
4. This system provides the ability to connect to internal fracture fixation hardware, further enhancing the augmentation of fracture fixation.

FIG. 18a is a schematic representation of multiple delivery supplies as exemplified by 3 chambers of reservoirs of biomaterials for supplying the delivery system in an alternative embodiment of the present invention.

FIGS. 18b and 18c are cross sectional views showing the alternative embodiment of FIG. 18a in more detail where in this embodiment, the multiple reservoirs are provided in the form of more than two chambers in the cartridge 250; for instance, with three chambers 201,202,251 being provided in the cartridge 250 as shown in FIGS. 18b and 18c; of course, any number of reservoir supplies of biomaterials can be provided in the delivery system; for example by providing any number of chambers within the cartridge. FIG. 19 is bar chart depicting a comparison of the Injectability Force for Configuration 1 system with a new biomaterial (0 days old) and an expired biomaterial (+4 months old). Comparison of Configuration 1 and Configuration 4 systems using an expired biomaterial (+4 months old) only.

In summary, the system, device and method of the present invention comprises the following advantageous features:
1. A biomaterial delivery system comprising:
a dispenser device for dispensing biomaterial to a desired target site, the dispenser device including an actuator operable for actuating the delivery device; the device being adapted to engage with a reservoir containing the biomaterial (s); a mixer device for mixing the biomaterial(s) and any activator that may be required; and
a conduit for transferring the biomaterial(s) from the mixer device to the desired target site.
2. A biomaterial delivery system as in statement 1 wherein the conduit comprises a cannula or cannulated fracture fixation device.
3. A biomaterial delivery system as in statement 1 or 2 wherein the dispenser device comprises a means operable to discharge the biomaterial and any activation component from the reservoir into the mixer device and the conduit for delivery to the desired target site.
4. A biomaterial delivery system as in any one of the preceding numbered statements wherein the dispenser device comprises a reservoir for containing biomaterial.

5. A biomaterial delivery system as in any one of the preceding numbered statements wherein the reservoir comprises a cartridge for containing the biomaterial.

6. A biomaterial delivery system as in any one of the preceding numbered statements wherein the delivery device comprises a reservoir locking means for engaging with the reservoir and holding the reservoir in position on the delivery device.

7. A biomaterial delivery system as in statement 6 wherein the locking means comprises a slot adapted to engage with the cartridge.

8. A biomaterial delivery system as in any one of the preceding statements wherein the delivery device comprises a delivery gun and housing of the delivery gun pivotally supports an actuation trigger which is operable to advance a plunger drive mechanism in order to release the biomaterial from the cartridge.

9. A biomaterial delivery device as in statement 8 wherein once the trigger is actuated, a gripper plate engages with the drive mechanism and the drive mechanism advances the plunger(s).

10. A biomaterial delivery system as in any one of the preceding statements wherein the dispenser gun has a release button that allows a user to manually retract the plungers if required in order to remove the cartridge.

11. A biomaterial delivery system as in any one of the preceding statements wherein the reservoir comprises a cartridge unit comprising a first chamber providing containment of the biomaterial; and optionally comprising a second chamber for providing containment of a second material so that the cartridge is configured to contain the biomaterial and second material separately from each other until required at the site of the surgery.

12. A biomaterial delivery system as in statement 11 wherein the cartridge comprises two or more chambers for containing the biomaterial(s) and activator component(s) separately from each other until required at the site of the surgery.

13. A biomaterial delivery system as in statement 11 wherein the cartridge unit comprises three or more chambers depending on the biomaterial formulation.

14. A biomaterial delivery system as in any one of statements 11 to 14 wherein each chamber is in the form of a generally cylindrical cross section having an elongate longitudinal axis, and the or each cylinder having proximal and distal ends.

15. A biomaterial delivery system as claimed in any one of statements 11 to 15 wherein the or each cylinder comprises a piston, which, optionally, is generally positioned at the proximal end of the cartridge.

16. A biomaterial delivery system as in statement 15 wherein a stop member is located at the proximal end on the cylindrical wall of the cartridge to prevent the piston/plunger from being pushed outside the housing.

17. A biomaterial delivery system as claimed in statements 11 to 17 wherein sealing means is provided at the proximal end of the cartridge to support containment, where the surgeon can remove this seal before usage of the device.

18. A biomaterial delivery system as claimed in any one of the preceding statements wherein the distal end of the cartridge comprises feeding channels that are in fluid communication with the mixer.

19. A biomaterial delivery system as claimed in statement 18 wherein the number of channels corresponds with the number of chambers included in the cylinder unit of a particular embodiment of the device so that each chamber has its own channel in fluid communication with the mixer.

20. A biomaterial delivery system as claimed in an earlier statement wherein each of the channels comprises removeable sealing means preferably selected from one or more of the following: ultrasonic weld, foil seal, bung cap or by similar sealing device in order to provide containment before usage whereby the seal is configured to be removable from each of the channels in order to expose the contents of any of the channels before placement of the mixer to the desired site of delivery of the biomaterial.

21. A biomaterial delivery system as in an earlier statement wherein all components of the cartridge are manufactured using medical grade polymeric materials that have moisture/oxygen barrier characteristics as required by the formulation of the biomaterial to be delivered.

22. A biomaterial delivery system as in any one of the preceding statements wherein the mixer device comprises a cylindrical shaft having proximal and distal ends. There may be mixing elements provided in the mixer device. Alternatively, there may be no mixing elements comprised in the mixer device and instead, in this embodiment, mixing elements may be provided in the conduit for transporting the biomaterial(s) to the desired delivery site. The conduit for transporting the biomaterial(s) from the mixer device to the desired delivery site comprises a cannula or an internal fracture fixation device, and the conduit is configured by having connectors at the proximal end, to enable sealing engagement with the mixer device.

23. A biomaterial delivery system as claimed in statement 22 wherein the mixer device is configured for engagement at one end thereof, with the reservoir of biomaterial(s) and at the other end, with the conduit for transferring the biomaterial(s) to the desired delivery site.

24. A biomaterial delivery system as in statement 23 wherein, at the proximal end of the mixer device, the mixer device comprises a connector, adapted for engagement with the reservoir which optionally is in the form of a cartridge so as to allow the mixer to be connected to the reservoir to support the delivery of the components to the mixing section of the mixer.

25. A biomaterial delivery system as in statement 23 wherein the interface between the cartridge and mixer is designed so that a high quality seal is provided to prevent loss/leakage of the biomaterials or activator components.

26. A biomaterial delivery system as in statement 25 wherein at the distal end of the mixer, a locking means is provided and is configured for connection of the delivery system to a cannulas or other internal fracture fixation devices such as cannulated screws, nails and pins.

27. A biomaterial delivery system as in statement 25 wherein the mixer device comprises a mixing section between the proximal and distal end of the mixer device.

28. A biomaterial delivery system as in statement 27 wherein the mixing section comprises mixing elements configured to enable mixing of different viscosity biomaterials.

29. A biomaterial delivery system as in statement 28 wherein the mixing elements comprise a helical baffle or similar mixing elements.

30. A biomaterial delivery system whereby the biomaterial expiry (shelf life) is maximized by using the Configuration 2, 3 and 4 of the system as described herein.

31. A delivery system of the present invention wherein the biomaterial(s) are mixed by moving the material(s) along the mixer device which may comprise moving the material(s) through a mixing shaft that may be provided in the mixer device of one embodiment where the biomaterial and activator component are brought together. At this stage, the curing (setting) reaction is initiated, forming the required material at exactly the point of dispensing, allowing the surgeon to have full control of the setting reaction.

In one embodiment, the mixing elements may be located throughout substantially the full length of the mixer shaft; and may or may not be fixated to the proximal end of the mixer. This arrangement (Configuration 1) is typically used for biomaterials that have low viscosities and delivery device in this embodiment, can mix the components up to 65,500 times.

32. A biomaterial delivery system wherein, for high viscosity biomaterials, the mixer shaft may contain a lower number of mixing elements. In an alternative embodiment, the mixing elements may be arranged such that they are not fixed but are free to move, preferably in both longitudinal directions, along the full length of the mixer shaft or substantially along the length of the mixer shaft. In a further alternative embodiment, the mixing elements may be fixated to the proximal end of the mixer shaft (Configuration 2). When high viscosity biomaterials and activator components are dispensed into the mixer shaft containing the mobile mixing elements, the biomaterials and activator components have time to partly mix before being pressurized against the mixing elements at the distal end, which completes the mixing process. This helps to reduce the viscosity of the components, therefore, allowing them to flow more freely through the mixing elements. By doing so, the injectability force is reduced significantly, thus, enhancing the usability of the device.

33. A delivery device for high viscosity biomaterials comprising a small number of mobile mixing elements in an extended mixer shaft. Once the components enter the mixing shaft from the cartridge, they have additional time to partly mix before reaching the mixing elements at the distal end. This helps to reduce the viscosity of the components further, allowing them to flow more freely through the mixing elements.

34. In a further alternative embodiment, (Configuration 4) for extremely high viscosity biomaterials, the mixing elements are removed completely from the mixing shaft. In this embodiment, the components are mixed at a later stage, such as in the cannula device or other internal fracture fixation devices such as cannulated screws, nails and pins. By removing the mixing elements entirely from the mixer, this allows the biomaterial and activator components to partly but sufficiently mix and reduce their viscosities before exiting the mixer. The cannula is comprised of a cylindrical tube having both proximal and distal ends with an internal diameter of 2.55 mm and an outer diameter of 3.5 mm (or as otherwise specified by the biomaterial to be implanted). At the proximal end, the cannula has a male Luer lock which can fit securely on to the female Luer lock of the mixer. In addition, this end of the cannula includes two wings to allow the surgeon to secure the cannula to the mixer with ease. At the distal end of the cannula, this is where the final mixed biomaterial is dispensed from the complete device into the target area. The distal end can have a round nose tip with an opening of 1.5 mm or a flat tip with an opening of 2.5 mm (or as otherwise specified by the biomaterial to be implanted). A flat tip is typically used where the mixing elements are included in the mixer. When there are no mixing elements in the mixer, the mixing elements are typically placed in the cannula. A round nose tip cannula is used in this case to prevent the mixing elements from being moved out of the cannula housing as the biomaterials and activator components are being dispensed. The purpose of moving the mixing elements from the mixer to the distal end of the cannula is to allow the biomaterials and activator components to come together for an extended period of time prior to reaching the elements. This helps to reduce the viscosity by partially mixing the components, therefore; allowing them to flow more freely through the mixing elements. In terms of design, the reduction of the internal diameters from the mixer to the cannula supports the partial mixing process, due to the turbulence created at this section. In addition, the reduction of the internal diameter increases the velocity of the components, thus, reducing the overall pressure in contrast to the alternative systems previously mentioned. One of the principle design features that generates pressure in the previous mentioned systems is the positioning of the mixing elements. By having them positioned at an early stage in the process, this restricts viscosity reduction of the components while creating a flow barrier prior to reaching the reduced internal diameters between the mixer and cannula. This reduces the velocity of the components in the system, therefore; increasing the pressure. The working length of the cannula can vary in size depending on the viscosity of the biomaterial and the surgeon requirements. Having a cannula with a longer working length allows the biomaterial and activator component more time to mix before being dispensed to the target area and this applies for all aforementioned systems. In the system where the mixer contains no mixing elements and the cannula contains mixing elements at the distal end, a longer cannula allows the viscosity of the components to decrease substantially, therefore; enhancing the injectability for the surgeon.

35. The surgeon has the option to connect the mixers of Configurations 1-4 to the cannulas for bone void filling or to multiple internal fracture fixation devices for augmented fixation trauma indications (i.e. to be used without the cannula component).

36. For the internal fracture fixation devices such as screws, pins, nails or similar, they have the ability to be connected to each mixer configurations by the use of a sheath and sheath adaptor (provided with the internal fracture fixation device). At the distal end of the sheath is a standard screwing thread that allows the surgeon to fasten the sheath onto the internal fracture fixation device by screwing in a clockwise direction. At the proximal end of the sheath is a female Luer lock that permits connection of the sheath to the sheath adaptor. The distal end of the sheath adaptor is placed inside the proximal end of the sheath. When the sheath adaptor is fastened in place by screwing in a clockwise direction, the distal end of the device protrudes past the distal end of the sheath and into the cannula opening of the proximal end of the internal fracture fixation device. At the proximal end of the sheath adaptor is a male Luer lock that allows the overall device (sheath, sheath adaptor and internal fracture fixation device) to be connected to any of the mixers in configurations 1-4.

37. With the mixer in configurations 1-3, mixing of the biomaterials with the activator components is completed prior to entering the sheath adaptor and internal fracture fixation device.

38. For the mixer in Configuration 4, the biomaterials and activator components are mixed to completion upon entering the internal fracture fixation device. In this design, the complete mixing process is further in the system as the components travel through the various contours of the sheath adaptor and the cannulated internal fracture fixation device.

39. These contours create sufficient turbulence to homogeneously mix the components to provide the required setting time and compressive strength characteristics.

40. A method of delivering biomaterial to a desired site using the biomaterial delivery system involves the following steps:
(i) Assembling the biomaterial delivery system by carrying out the following steps:
(ii) Attaching the cartridge (with two or more chambers) to the dispenser gun;
(iii) Attaching the mixer (with Luer or similar lock fitting) to the cartridge; and
(iii) Attaching the cannula or internal fracture fixation devices (screws, nails and pins) to the mixer.

41. A method of delivering biomaterial to a desired site as in the statement above wherein following assembly of the system using the steps of the method of above statement, the cement can be delivered by actuating the device where typically, the actuator comprises an actuator trigger operable by hand, so that typically, by squeezing the trigger to actuate the delivery device, the biomaterial and activation component(s) pass through the mixer and cannula (if required), initiating the curing reaction.

42. A method as claimed in statement 40 wherein at step (iii), the sheath is fastened onto the internal fracture fixation device by screwing the sheath in a clockwise direction. The distal end of the sheath adaptor is then placed inside the sheath from the top end The internal fracture fixation device may comprise a conduit which may be extending along an elongate longitudinal axis of the internal fracture fixation device so that the internal fracture fixation device is in fluid communication with a reservoir of biomaterial(s) so that, in use, the biomaterial(s) can be delivered from the reservoir through the mixer device and through the conduit of the internal fracture fixation device. The conduit may also be provided axially about the internal fracture fixation device by providing apertures axially about the circumference of the internal fracture fixation device, optionally, axially about the ridges of the threads of the internal fracture fixation device where the internal fracture fixation device comprises screw threaded arrangement, partially or extending fully along the longitudinal axis of the internal fracture fixation device.

All embodiments/configurations of the mixing system have the advantage that the system allows the components to mix several times before targeted delivery to ensure the desirable performance criteria have been met.

The words, comprises/comprising, when used in this specification are to specify the presence of stated features, integers, steps or components but do not preclude the presence or addition of one or more other features, integers, steps, components or groups thereof.

The invention claimed is:
1. A biomaterial delivery system comprising:
a dispenser device for dispensing a biomaterial to a desired target site, the dispenser device including an actuator operable for actuating the dispenser device; the dispenser device further including a reservoir for containing the biomaterial, wherein the reservoir comprises a cartridge comprising a first chamber providing containment of the biomaterial and a second chamber for providing containment of a second material so that the cartridge is configured to contain the biomaterial and second material separately from each other until required at the site of the surgery, wherein each chamber comprises a piston positionable adjacent to a proximal end of the cartridge, and wherein a stop member is located at the proximal end of the cartridge to prevent the piston from being pushed outside the cartridge;
a mixer device attachable to the reservoir and structured for mixing the biomaterial and any activator that may be required, the mixer device including a mixing shaft and one or more mixing elements disposed within an interior cavity of the mixing shaft; and
a conduit attachable to the mixer device such that the conduit is in fluid communication with the mixer device, the conduit structured for receiving the mixed biomaterial from the mixer device and transferring the mixed biomaterial to the desired target site, wherein the conduit comprises a cannulated fracture fixation device.

2. The biomaterial delivery system as claimed in claim 1 wherein the cannulated fracture fixation device comprises an orthopedic screw, nail, or pin.

3. The biomaterial delivery system as claimed in claim 1 wherein the actuator comprises an actuation trigger operable to discharge the biomaterial and any activation component from the reservoir into the mixer device and the conduit for delivery to the desired targe site.

4. The biomaterial delivery system as claimed in claim 1 wherein the delivery device comprises a reservoir locking mechanism for engaging with the reservoir and holding the reservoir in position on the delivery device, wherein the locking mechanism comprises a slot adapted to engage with the cartridge.

5. The biomaterial delivery system as claimed in claim 1 wherein each chamber includes a generally cylindrical cross section having an elongate longitudinal axis.

6. The biomaterial delivery system as claimed in claim 1 wherein a seal is provided at the proximal end of the cartridge to support containment, and wherein the seal is configured to be removed before usage of the device.

7. The biomaterial delivery system as claimed in claim 1 wherein a distal end of the cartridge comprises feeding channels that are in fluid communication with the mixer device.

8. The biomaterial delivery system as claimed in claim 7 wherein the number of channels corresponds with the number of chambers so that each chamber has its own channel in fluid communication with the mixer device.

9. A biomaterial delivery system comprising:
a dispenser device for dispensing a biomaterial to a desired target site, the dispenser device including an actuator operable for actuating the dispenser device, the dispenser device further including a reservoir for containing, the biomaterial, the reservoir comprising a cartridge including a first chamber for providing containment of the biomaterial and a second chamber for providing containment of a second material, each chamber comprising a piston positionable adjacent to a proximal end of the cartridge, wherein a stop member is located at the proximal end of the cartridge to prevent the piston from being pushed outside the cartridge;
a mixer device including a mixing shaft, an inlet attachable to and in fluid communication with an outlet of the reservoir, an outlet including a leer lock, and one or more mixing elements disposed within an interior channel of the mixing shaft between the inlet and the outlet, the one or more mixing elements configured for mixing the biomaterial and any activator that may be required prior to reaching the outlet of the mixer device; and
a conduit including an inlet attachable to the bier lock at the outlet of the mixer device such that the conduit and the mixer device are in fluid communication, the conduit structured for receiving the mixed biomaterial from the mixer device and transferring the mixed biomaterial to the desired target site, wherein the conduit comprises an internal fracture fixation device.

10. The biomaterial delivery system as claimed in claim 9 wherein the fracture fixation device includes a hollow bore for transferring the biomaterial from the reservoir to a desired delivery site.

11. The biomaterial delivery system as claimed in claim 10 wherein the internal fracture fixation device is adapted to be connected to the mixer device by the use of a sheath and a sheath adaptor, wherein at a distal end of the sheath, a connector is provided for engaging the sheath onto the internal fracture fixation device.

12. A biomaterial delivery system comprising:
a dispenser device for dispensing a biomaterial to a desired target site, the dispenser device including an actuator operable for actuating the dispenser device, the dispenser device further including a reservoir for containing the biomaterial, the reservoir comprising a cartridge including a first chamber with a first outlet feeding channel and a second chamber with a second outlet feeding channel, each chamber comprising a piston positionable adjacent to a proximal end of the cartridge, wherein a stop member is located at the proximal end of the cartridge to prevent the piston from being pushed outside the cartridge;
a mixer device extending from a proximal inlet end to a distal outlet end, the proximal inlet end including a first inlet feeding channel and a second inlet feeding channel and the distal outlet end including a luer lock connection, the proximal inlet end directly attachable to a distal outlet end of the reservoir such that the first and second inlet feeding channels of the mixer device engage the respective first and second outlet feeding channels of the reservoir, thereby forming an interface that provides a fluid seal, the mixer device including a mixing shaft and one or more mixing elements disposed within an interior channel of the mixing shaft between the proximal inlet end and the distal outlet end, the one or more mixing elements configured for mixing the biomaterial and any activator that may be required prior to reaching the distal outlet end of the mixer device; and
a conduit including a proximal inlet attachable to the liter lock connection and in fluid communication with an outlet at the distal outlet end of the mixer device, the conduit structured for receiving the mixed biomaterial from the mixer device and transferring the mixed biomaterial to the desired target site, wherein the conduit comprises an internal fracture fixation device including a plurality of longitudinally spaced fenestrations extending through an outer surface of the internal fracture fixation device.

13. The biomaterial delivery system as claimed in claim 12, wherein the mixer device includes a guide notch on the mixing shaft that is alignable with the reservoir to ensure proper connection of the mixer device to the reservoir.

14. The biomaterial delivery system as claimed in claim 12, wherein the first chamber is configured to contain the biomaterial and the second chamber is configured to contain the activator.

15. The biomaterial delivery system as claimed in claim 14, wherein the first and second inlet feeding channels are structured to receive the biomaterial and the activator in an unmixed state and transfer the biomaterial and the activator to the interior channel of the mixing shaft for mixing therein.

* * * * *

UNITED STATES PATENT AND TRADEMARK OFFICE
CERTIFICATE OF CORRECTION

PATENT NO. : 11,160,595 B2
APPLICATION NO. : 15/566465
DATED : November 2, 2021
INVENTOR(S) : Insley et al.

It is certified that error appears in the above-identified patent and that said Letters Patent is hereby corrected as shown below:

In the Claims

Column 23, Line 55, Claim 1, delete "device;" and insert --device,-- therefor

Column 24, Line 20, Claim 3, delete "targe" and insert --target-- therefor

Column 24, Lines 46-47, Claim 9, delete "containing," and insert --containing-- therefor Column 24, Line 57, Claim 9, delete "leer" and insert --luer-- therefor Column 24, Line 63, Claim 9, delete "bier" and insert --luer-- therefor Column 26, Line 10, Claim 12, delete "liter" and insert --luer-- therefor Signed and Sealed this
Twenty-first Day of December, 2021

Drew Hirshfeld
*Performing the Functions and Duties of the
Under Secretary of Commerce for Intellectual Property and
Director of the United States Patent and Trademark Office*